(12) United States Patent
Holtzapple et al.

(10) Patent No.: US 6,395,926 B1
(45) Date of Patent: May 28, 2002

(54) PROCESS FOR RECOVERING LOW-BOILING ACIDS

(75) Inventors: Mark T. Holtzapple, College Station; Richard R. Davison, Bryan, both of TX (US)

(73) Assignee: Texas A&M University System, College Station, TX (US)

( * ) Notice: Subject to any disclaimer, the term of this patent is extended or adjusted under 35 U.S.C. 154(b) by 0 days.

(21) Appl. No.: 09/882,853

(22) Filed: Jun. 15, 2001

Related U.S. Application Data

(62) Division of application No. 09/469,245, filed on Dec. 22, 1999, now Pat. No. 6,262,313, which is a division of application No. 08/885,896, filed on Jun. 30, 1997, now Pat. No. 6,043,392.

(51) Int. Cl.[7] .................. C07C 51/00; C07C 59/08

(52) U.S. Cl. ............... 562/513; 562/580; 562/589; 562/606; 44/385

(58) Field of Search ................. 562/513, 580, 562/589, 606; 44/385

(56) References Cited

U.S. PATENT DOCUMENTS

| | | | | |
|---|---|---|---|---|
| 4,282,323 A | * | 8/1981 | Yates ................. | 435/140 |
| 4,405,717 A | * | 9/1983 | Branko Urbas ...... | 435/140 |
| 4,898,644 A | * | 2/1990 | Van Horn ............ | 203/15 |
| 5,969,189 A | * | 10/1999 | Holtzapple et al. .. | 568/397 |

* cited by examiner

*Primary Examiner*—Sreeni Padmanabhan
(74) *Attorney, Agent, or Firm*—Baker Botts L.L.P.

(57) ABSTRACT

The invention provides a method for recovering low-boiling acids from a concentrated solution of the calcium salt of the acid by treating the concentrated solution of calcium salts of the low-boiling acids with a high molecular weight tertiary amine and carbon dioxide.

8 Claims, 16 Drawing Sheets

PROCESS FOR RECOVERING LOW-BOILING ACIDS

This is a divisional application of U.S. patent application Ser. No. 09/469,245 filed Dec. 22, 1999, now U.S. Pat. No. 6,262,313 which was a divisional application of U.S. patent application Ser. No. 08/885,896, filed Jun. 30, 1997 now U.S. Pat. No. 6,043,392.

BACKGROUND OF THE INVENTION

1. Field of the Invention

This invention provides a process for converting biomass to useful chemicals or fuels, by anaerobic fermentation of biomass and recovery of useful products from the fermentation medium. By alternative arrangement of the process steps of this invention, a variety of products (i.e. organic acids, ketones, aldehydes, and alcohols) may be produced from biomass. These products are made from salts of the organic acids (e.g., acetate, propionate, butyrate, lactate) that are the primary fermentation products of the fermentation.

2. Review of Related Art

Organic acids are important chemicals of commerce. Historically, organic acids were produced from animal fat or vegetable oil sources or from petroleum sources in substantially nonaqueous systems. More recently, organic acids have been identified as among the most attractive products for manufacture from biomass by fermentation. Biomass can be defined as any animal- or plant-based material of carbohydrate, protein or fat composition. Among the readily available sources of biomass are municipal solid waste (MSW) and sewage sludge (SS). At present, great expenditures of public funds are used to dispose of such wastes, including costs involved in treatment, transport, incineration, or dumping in landfills or oceans. The recovery of valuable products from biomass such as MSW and SS could recover the costs of disposal as well as reduce reliance on nonrenewable fossil fuel resources which serve as feedstock for most industrial organic acid production. Fermentation, therefore, can convert renewable organic materials, now considered a costly waste, into valuable chemical commodities.

However, the acids are produced by the fermentation in dilute aqueous solutions, and recovery of the acids in pure form involves separation from a large quantity of water. This recovery introduces significant operating expense into the process, while the physical plant required to handle the large volumes of solution introduces significant capital expense. The combination of capital and operating expense has, until now, made production of organic acids from biomass uneconomical. Thus, there remains a need for a process that combines unit operations for fermentation, concentration and recovery of organic acids to take advantage of potential synergies obtainable from integrating these processes, thereby generating an economical process for conversion of biomass to useful products.

Ketones, aldehydes, and alcohols predominately are produced from petroleum and natural gas. Because fossil fuels are a finite resource, it is desirable to identify processes that use renewable resources, such as biomass. Biomass-based alcohol production is currently practiced using corn as feedstock; however, because corn has alternative use as food, the feedstock is necessarily costly making the ethanol product expensive. Experimental technologies are being developed in which extracellular enzymes, such as cellulase and hemicellulase, are added to lignocellulosic biomass to produce sugars that are subsequently fermented to ethanol. The primary challenges of this technology are to develop inexpensive sources of enzyme and to develop organisms that can ferment the variety of sugars to ethanol with high yields.

The technology described herein overcomes problems associated with the competing biomass-based technologies by employing mixed cultures of microorganisms that convert the many components of biomass (e.g., cellulose, hemicellulose, pectin, sugar, protein, fats) to organic acids that are subsequently converted to ketones, aldehydes, and alcohols using a variety of chemical steps. Further, the microorganisms produce their own enzymes, thus avoiding the need to add costly extracellular enzymes.

SUMMARY OF THE INVENTION

It is an object of this invention to provide a process for converting salts of volatile fatty acids, produced by anaerobic fermentation of biomass, into liquid fuels.

It is an object of this invention to provide an improved method for converting biomass to organic acids, ketones, aldehydes, and alcohols.

These and other objects are accomplished by one or more of the following embodiments of this invention.

In one embodiment, this invention provides a method for thermally converting volatile fatty acid (VFA) salts to ketones which comprises the steps of precipitating metal salts of volatile fatty acids (VFAs) from the fermentation liquor of an anaerobic fermentation, then recovering and drying precipitated metal salts of VFAs, mixing dry metal salts of VFAs with a heat transfer agent, preferably steel balls, glass balls or ceramic balls, more preferably hollow balls that are filled with a substance that melts at the temperature of thermal decomposition of VFAs, in an evacuated container, the hot heat transfer agent being sufficient to raise the temperature of the metal salts of VFAs to cause thermal decomposition, with the resulting formation of ketone-containing vapor and metal salt of carbonate; and then separating the ketone-containing vapor from the metal carbonate salt and heat transfer agent, and recovering liquid ketones by condensing the ketone-containing vapor. Preferably, the metal salts of VFAs are alkali metal or alkaline earth salts, more preferably, calcium salts.

In another embodiment, this invention provides a method for recovering low-molecular-weight aldehydes and ketones from fermentation liquor produced by anaerobic fermentation of biomass, which method comprises the steps of (a) concentrating salts of volatile fatty acids (VFAs) from fermentation liquor produced by anaerobic fermentation of biomass; (b) precipitating and drying the calcium salts of VFAs; (c) adding salts of formic acid; (d) mixing the dry calcium salts of VFAs and formic acid with a heat transfer agent, thereby causing thermal decomposition of the calcium salts of VFAs to form ketone-containing and aldehyde-containing vapor and calcium carbonate; (e) maintaining a vacuum in the container by condensing ketones and aldehydes from the ketone-containing and aldehyde-containing vapor and removing non-condensable vapor from the container; (f) removing a mixture of calcium carbonate and heat transfer agent from the container; and (g) separating the heat transfer agent from the calcium carbonate, reheating and recycling the heat transfer agent, and calcining the calcium carbonate in a lime kiln. Optionally, the separated calcium carbonate could be recycled directly to the fermentor without further processing.

In yet another embodiment, this invention provides a mixture of secondary alcohols produced from ketones obtained from precipitated calcium salts of volatile fatty acids (VFAs) produced by anaerobic fermentation of biomass; drying the precipitated calcium salts of VFAs; mixing dry calcium salts of VFAs with a hot heat transfer agent in an evacuated container, thereby causing thermal decomposition of the calcium salts of VFAs to form ketone-containing vapor and calcium carbonate; separating the ketone-containing vapor from the calcium carbonate and heat transfer agent by condensing a mixture of ketones from the ketone-containing vapor; and finally hydrogenating the mixture of ketones recovered from the fermentation liquor. Alternatively, a mixture of primary and secondary alcohols can be produced can be produced by adding a calcium salt of formic acid to the evacuated container.

In an alternative embodiment, volative fatty acids (VFAs) can be produced by (a) anaerobically digesting biomass to produce a dilute solution of salts of VFAs; (b) concentrating the VFA salts; (c) adding a low-molecular-weight tertiary amine and carbon dioxide causing calcium carbonate to precipitate; (d) adding a high-molecular-weight tertiary amine to the solution from step c; (e) distilling off the low-molecular-weight tertiary amine; and (f) thermally converting the high-molecular-weight tertiary amine/VFA complex to high-molecular-weight amine and VFA. Alternatively, lactic acid can be produced by thermally converting a low-molecular-weight amine/lactic acid complex to low-molecular-weight amine and lactic acid.

DETAILED DESCRIPTION OF THE INVENTION

The process of this invention produces low-molecular-weight organic acids, especially volatile fatty acids, by anaerobic fermentation of biomass. A number of process variations are contemplated within this invention, but all the processes have three common sections of the plant: fermentation, concentration, and recovery.

Figure 1:
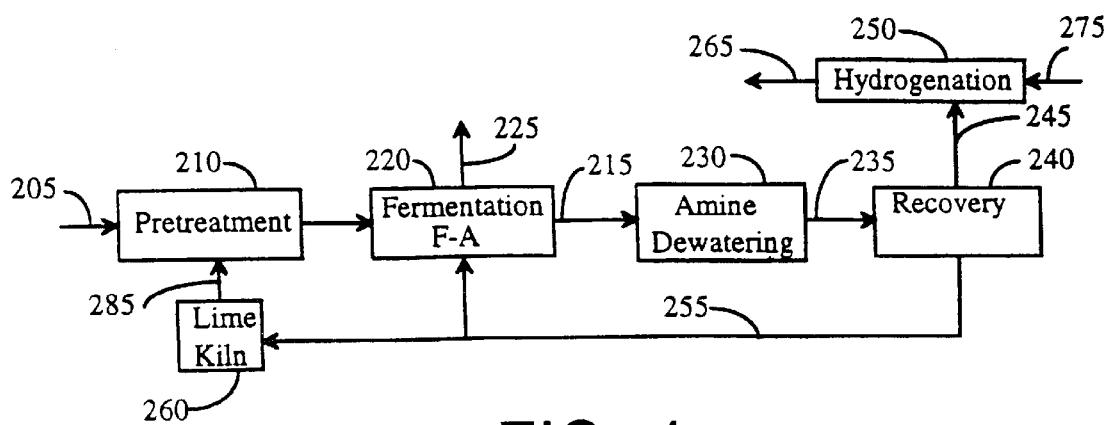
FIG. 1 is a schematic diagram of a process for converting biomass to liquid secondary alcohol fuel (Fermentation Method F-A plus Recovery Method R-A).

An overall schematic diagram of a process for producing mixed secondary alcohols is shown in FIG. 1. Biomass 205 is first passed through pretreatment stage 210, and then fed into fermentation stage 220 where the pretreated biomass is converted to VFA salts 215 and undigested residue 225. Fermentation liquor containing VFA salts 215 is transferred to amine dewatering stage 230 where water is extracted, thus concentrating the VFA salts to approximately 20% in concentrated stream 235. Undigested residue 225 from the fermentation stage is discarded or perhaps burned for process heat.

In recovery stage 240, concentrated solution of VFA salts 235 is evaporated to dryness and thermally converted to mixed ketones 245 and calcium carbonate 255. Ketones 245 may be further processed in hydrogenation stage 250 where they are hydrogenated with hydrogen gas 275 using a suitable catalyst (e.g., Raney nickel) to produce mixed alcohols 265 useful as fuels. Alternatively, if a concentrated acid stream is the desired product, concentrated solution of VFA salts 235 may be processed as described below to "spring" the acids from the salt solution. The resultant acid stream may be used directly, rather than processing through the thermal decomposition and hydrogenation steps. Calcium carbonate 255 can either be recycled to fermentation stage 220 to neutralize acids produced by the fermentation, or burned in lime kiln 260 to produce lime 285 which may be used in pretreatment stage 210. Alternatively, rather than adding calcium carbonate 255 to Fermentor 220, lime 285 may be added in order to maintain a higher pH in fermentor 220.

Volatile fatty acids as contemplated by this invention are saturated aliphatic carboxylic acids with relatively low carbon number, such as acetic, propionic and butyric acids (carbon number 2–4). As contemplated, volatile fatty acids include all aliphatic carboxylic acids produced by "acid-forming" bacteria under anaerobic fermentation conditions. These carboxylic acids boil at relatively low temperature, and are therefore, designated "volatile." Table 1, showing the boiling points for normal alkyl carboxylic acids at atmospheric pressure, is given below:

TABLE 1

| Carbon No. | Acid | B.P. (° C.) |
|---|---|---|
| 2 | acetic | 118 |
| 3 | propionic | 141 |
| 4 | butyric | 164 |
| 5 | valeric | 184 |
| 6 | caproic | 202 |
| 7 | enthantic | 223 |
| 8 | caprylic | 238 |
| 9 | pelargonic | 253 |
| 10 | capric | 268 |

Recovery of Chemicals and Fuels

This patent disclosure describes a family of processes all based on a common method of biomass conversion by anaerobic fermentation. The processes are divided into three sections: fermentation, concentration, and recovery. Variants in each section of the process are described in more detail below. Each of these sections of the overall process have been tested independently, some on very large scales. Further optimization of the overall process may be accomplished for particular biomass feedstocks and environmental situations (e.g., nearby sources of, or uses for, excess process energy) based on the considerations described herein. Such optimization is easily within the skill of the art.

Fermentation as described herein may be carried out by a pure culture of microorganisms or by a mixed culture. Mixed culture fermentation is described below in Fermentation Method F-A, using adventitiously collected acid-forming bacteria. Fermentation Method F-B produces both ethanol and salt of organic acids using pure or mixed cultures of bacteria, one of which must be cellulolytic. Fermentation Method F-C uses pure cultures of lactic-acid-forming bacteria. While the cultures for these alternative fermentations are different, the various methods may use similar raw materials, similar fermentors, and the products may be recovered by similar methods (Recovery Methods A-E) except where specifically indicated otherwise.

Three types of fermentations are discussed herein:

|  | Products | | | | |
|---|---|---|---|---|---|
|  | acids | | | | alcohols |
| Fermentation | Acetic | Propionic | Butyric | Lactic | Ethanol |
| F-A | + | + | + | − | − |
| F-B | + | − | − | − | + |
| F-C | − | − | − | + | − |

Fermentation products are present in dilute aqueous solutions. Generally, there are about 30 kg of water per kg of product, and this large amount of water must be removed to recover and purify the fermentation products. Concentration of the organic acids produced by the fermentation (or separating them from the water in the fermentation medium) may be accomplished by a variety of different operations, include distillation, multiple-effect evaporation, vapor-compression, heat pumps, reverse osmosis, and extraction of the VFAs from the water. Selection of the particular unit operation will be made according to the guidelines provided herein, in view of the particular feedstocks, the desired product, and environmental situations (e.g., nearby sources of, or uses for, excess process energy). Such optimization is easily within the skill of the art.

Recovery from the inorganic salt of VFA may be accomplished by: (Recovery Method R-A) thermal conversion of VFA salts to ketones; (Recovery Method R-B) displacement of the inorganic cation by low-molecular-weight tertiary amines, followed by thermal decomposition of the amine carboxylate to release the acids and regenerate the amines; (Recovery Method R-C) successive replacement of the inorganic cation by low-molecular-weight, then high-molecular-weight tertiary amines, followed by thermal decomposition of the amine carboxylate; (Recovery Method R-D) displacement of the inorganic cation by high-molecular-weight tertiary amines, followed by thermal decomposition of the amine carboxylate to release the acids and regenerate the amines; and (Recovery method R-E) displacement of the inorganic cation by ammonia, then high-molecular-weight tertiary amines, followed by thermal decomposition of the amine carboxylate to release the acids and regenerate the amines. The first method produces ketones whereas the other four methods produce acids. The various recovery methods employ the chemicals listed below:

| Recovery | Product | Low-MW 3° Amine | High-MW 3° Amine | NH$_3$ |
|---|---|---|---|---|
| R-A | ketones | − | − | − |
| R-B | acids | + | − | − |
| R-C | acids | + | + | − |
| R-D | acids | + | + | − |
| R-E | acids | + | + | + |

The following chart shows which fermentation processes can be combined with the recovery processes:

|  | Recovery Processes | | | | |
|---|---|---|---|---|---|
| Fermentation Processes | R-A | R-B | R-C | R-D | R-E |
| F-A | + | + | + | + | + |
| F-B | + | + | + | + | + |
| F-C | − | + | − | − | − |

The method of this invention is particularly useful as part of a process for producing ketone or alcohol fuel from biomass. These products are made from calcium salts (e.g., acetate, propionate, butyrate) that are the primary fermentation products of anaerobic fermentation of biomass. A number of process configurations may be used, and suitable process components will be discussed in terms of fermentation, concentration, and recovery.

Pretreatment and Fermentation

Fermentation is generally an effective way to convert biomass feedstocks to organic acids. Cellulosic biomass is particularly attractive for this purpose. Rapier (M. S. Thesis, Texas A&M Univ., College Station, 1995) has determined that a mixture of 80% municipal solid waste (MSW) and 20% sewage sludge (SS) provides the optimal combination of energy and nutrients for a mixed culture of acid-forming microorganisms; therefore, this ratio was used in this study. However, cellulosic biomass sources generally need some degree of pretreatment for optimum conversion by fermentation.

Numerous treatments have been developed to enhance the enzymatic digestibility of lignocellulosic biomass including: physical (e.g., ball milling, two-roll milling), chemical (e.g., dilute-acid hydrolysis, alkali), physico-chemical (e.g., steam explosion, Ammonia Fiber Explosion), and biological (e.g., white-rot fungi). Alkaline treatment is particularly suitable for fermentations that produce acids because the acids produced in the fermentor will neutralize the alkali, thus allowing recovery of the treatment agent. Of the various alkalis that are effective (e.g., sodium hydroxide, ammonia), lime is attractive because of its low cost and compatibility with other process steps.

Compared to other alkalis, the literature on time treatments is relatively sparse. Most of the studies have been performed by animal scientists seeking simple, room-temperature treatments to enhance ruminant digestibility. Because the treatment temperature was low, their results were poor; leading to the general consensus that lime is not as effective as other alkalis. However, when the reaction temperature and other conditions are optimized, lime can be a very effective treatment agent. Recent lime treatment studies using extracellular enzymes to hydrolyze the biomass show that, compared to untreated biomass, lime-treated biomass has an enzymatic digestibility roughly ten-fold larger. Because of its low lignin content, herbaceous biomass requires only lime treatment. However, because of its high lignin content, woody biomass requires the addition of oxygen to partially oxidize the lignin and remove some of it from the biomass. In addition, woody biomass requires more severe time and temperature.

Lime treatment roughly doubles the ruminant digestibility of biomass. Furthermore, the digestibility within the ruminant is greater than that achieved with extracellular enzymes. This result suggests that an industrial process based on a mixed culture of microorganisms (analogous to rumen microflora) may have advantages over one based upon extracellular enzymes.

In a particular process example, biomass (e.g., bagasse, grass, municipal solid waste) is placed in a tank, and warm water is added from a recycle stream. Then lime is added to the biomass (typically 0.1 g $Ca(OH)_2$ per gram dry biomass). The lime/water/biomass slurry soaks for 1 to 24 hours while stirring. If the biomass particles are fairly coarse (i.e. greater than about 20 mesh), they may simultaneously be pumped through a colloidal mill (not shown) to grind them. However, it is preferred that the biomass be ground to a suitable particle size before lime addition. When the soak is complete, the lime water will be drained from the solid slurry. As a precaution to prevent excessively alkaline pH in the fermentor, more lime may be removed by leaching the biomass with recycle water. (Two vessels may be used for soaking and leaching, or these processes may actually occur in the same vessel.) Alternatively, rather than removing the lime, it can be neutralized in place by reacting it with carbon dioxide from the fermentors to form calcium carbonate.

Fermentation may be performed in liquid or semi-solid processes, in a single large fermentor, or a number of fermentors connected either in parallel or in series. The fermentation may be performed batchwise or in continuous or semi-continuous mode.

In one fermentation mode (F-A), the lime-treated biomass is slowly added to a fermentor where anaerobic organisms convert the biomass to organic acids. These organisms are a mixed culture that may be obtained from many sources (e.g., cattle rumen, soil, compost, or anaerobic sewage digesters). They produce a variety of products, but mainly acetic acid with lesser amounts of propionic and butyric acids. The ratio of these products depends on factors such as the microbial population, the pH, and temperature. Acetic acid dominates at temperatures above 55° C. As the organic acids are formed, the pH lowers. Typically, calcium carbonate or lime that was not recovered after the pretreatment process is used to neutralize the acids by forming calcium salts. The pH may be further regulated by adding more lime or calcium carbonate. Generally, a pH near 6.2 is preferred, but the pH can range from about 5.5 to 7.0.

Because asepsis is not required for mixed-culture fermentation of waste biomass (i.e. neither the feed nor vessels must be sterilized), recycle may be employed without risk of contamination. The fermentors can be operated in a continuous fashion. Cells may be recycled to maintain a high cell concentration in the fermentors which may reduce the required residence time. The solids concentration in the fermentor will usually be high (about 10–25%) to make the most efficient use of fermentor volume. If all the carbohydrates in the biomass were converted to organic acids, the concentration of organic acid salts would be about 8–20% which is much higher than can be tolerated by the microbes. To avoid this problem, the liquid may be constantly removed from the fermentors to maintain the organic acid salt concentration below about 3.4%. A number of methods could be employed to separate the solids from the liquid (e.g., filters, settlers). For example, the slurry could be pumped through a hydroclone in which the centrifugal force of the swirling fluid separates the solids from the liquid. The liquid will still have some particles, because the separation is not perfect; therefore, it can be further clarified by filtration through a sand filter, or similar device. When the sand filter is cleaned by backflushing, the solids are simply returned to the fermentors for further conversion to organic acids.

If a series of fermentors are employed, the biomass will travel through the fermentor train in essentially a plug flow. The carbohydrate content of the biomass will drop as it is converted to organic acids. Eventually, the solids will consist primarily of lignin, calcium carbonate, and cells. The cells can be recovered separately because they settle more slowly than the undigested solids and calcium carbonate. The remaining solids (lignin and calcium carbonate) can be burned in a lime kiln to supply process heat and convert the calcium carbonate into lime.

In an alternative configuration of this fermentation mode, a series of semi-solid fermentations has been operated using horizontal, stainless-steel cylinders, each with a center shaft having finger-like projections that extended nearly to the cylinder wall which "kneaded" the fermentor contents as the shaft rotated. Individual fermentor cylinders were operated in series with solids flowing countercurrently to the liquid, and solid/liquid separation was achieved by centrifuging the fermentor contents and decanting the liquid in an anaerobic hood. This countercurrent operation allowed high VFA concentrations to be generated in the fermentor receiving fresh, highly reactive solids. It also allowed high conversion because inhibition was low in the fermentor receiving fresh liquid.

Compared to rumen fermentations which typically require only a couple of days, the fermentor residence times in the above example were significantly longer due to the inhibition from the high VFA concentration (20–35 g/L versus 8–10 g/L), but because industrial-scale fermentors can be very inexpensive, the long residence time does not impose a severe economic penalty. The process time scales are similar to those for composting; thus, the process may be viewed as an anaerobic composting operation. The fermentor volume is proportional to the liquid residence time whereas the conversion is proportional to the solids residence time. Allowing both the VFA concentration and conversion to increase, conversions representing 85% of the maximum possible digestibility of a MSW/SS mixture were obtained.

In yet another alternative for this fermentation mode, the fermentation section of the process according to this invention will include more than one fermentation vessel, arranged for countercurrent flow of the biomass and the fermentation liquor. This arrangement is described in more detail in application Ser. No. 08/688,051, filed Jul. 31, 1996, entitled "Method and Apparatus for Producing Organic Acids. This arrangement includes a plurality of fermentor vessels, a countercurrent washing system, and solids transfer system.

The preferred shape of the fermentor vessel is the frustum of a pyramid. The fermentor is constructed by digging a pit and berming the earth. The slopes of the fermentor wall are preferably the "natural angle" that forms when gravel is piled (about 30°). The fermentor wall is lined with a geomembrane, gravel, and an abrasion-resistant liner. The top of the fermentor is covered to prevent gases from escaping into the atmosphere. Construction of individual fermentor tanks is described in more detail in U.S. application Ser. No. 08/688,051, entitled "Method and Apparatus for Producing Organic Acids," filed Jul. 31, 1996, incorporated herein by reference.

Figure 2A:
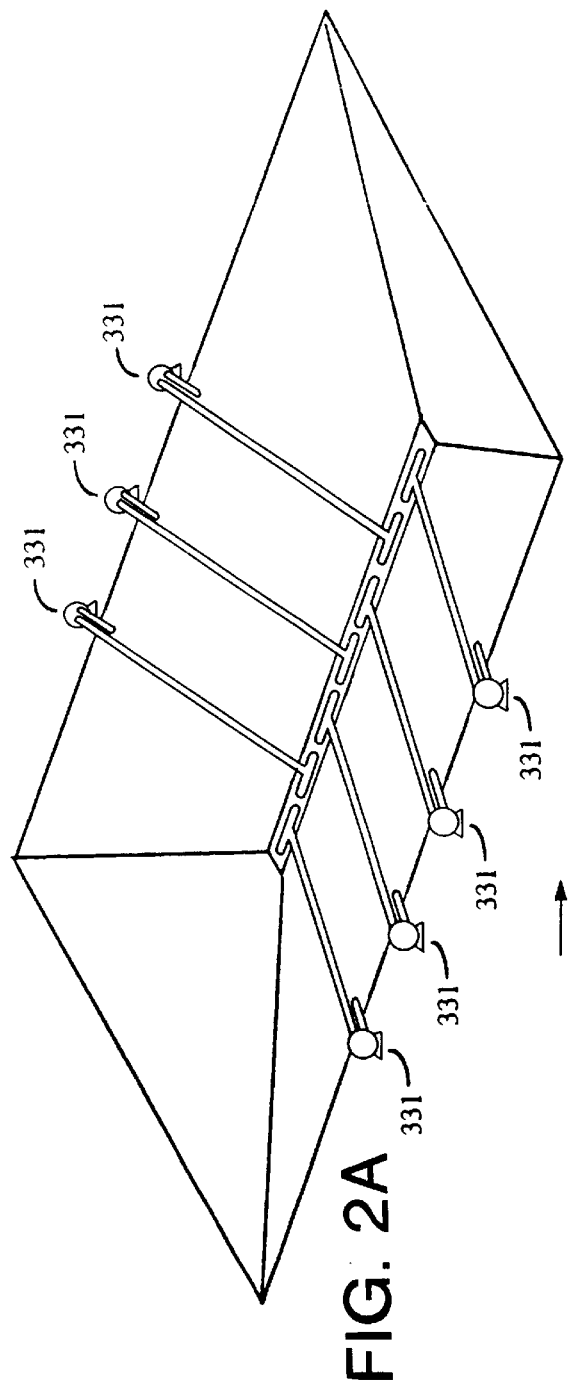
FIG. 2 shows a top view (A) and side view (B) of a biomass fermentor.
Figure 2B:
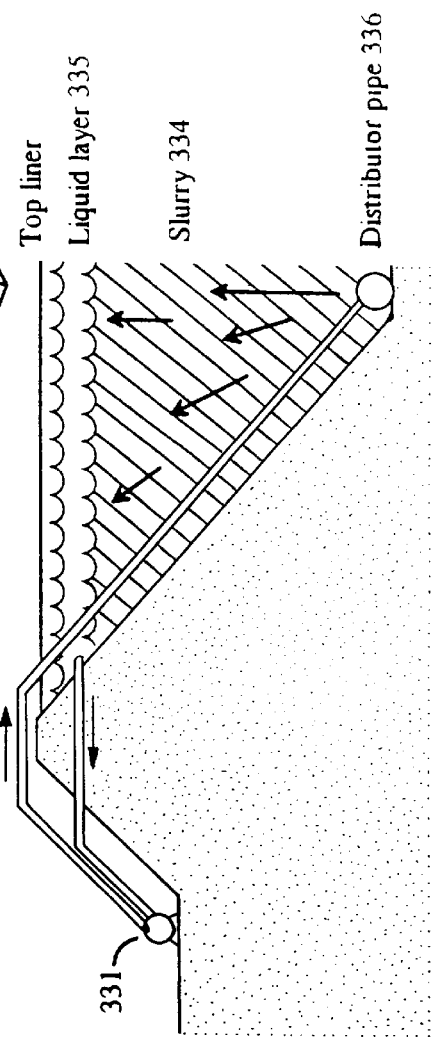

According to a preferred embodiment of the present invention shown in FIG. 2, liquid circulation provides agitation for the fermentor. The fermentor contents are a biomass/water slurry 334 with a layer of liquid 335 on top. A series of pumps 331 along the edge of the fermentor draws liquid from the top layer and pumps it back into the fermentor through a distributor pipe 336 located at the bottom. As the liquid flows up through the biomass, it eliminates pockets of high acid concentration that could inhibit biomass digestion. To create some mixing, liquid should preferably circulate through the fermentor about once every 12 hours, driven by fermentor circulation pumps 331.

In a related, preferred embodiment, the fermentation method of this invention provides liquid-piston pumps to transport solids through the fermentor complex. This mode does not require solids-transport pumps, thus eliminating a big capital expense and maintenance problem. This invention, in yet another preferred embodiment, also provides an inexpensive countercurrent washing system.

Figure 3:
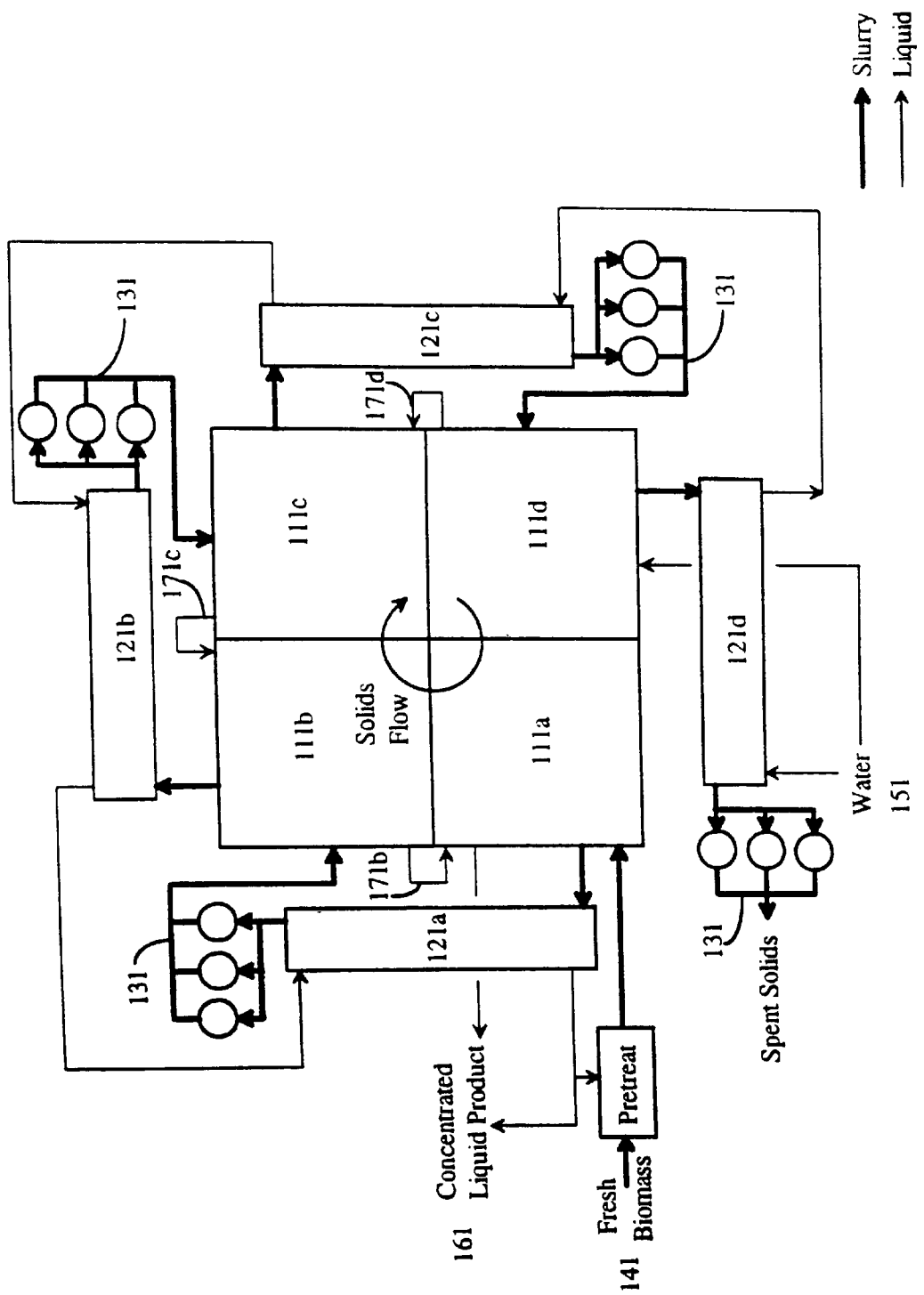
FIG. 3 is a schematic diagram of a preferred arrangement of four fermentor for countercurrent fermentation of biomass, top view.

FIG. 3 shows an aerial view of a preferred mode having four CSTR fermentors 111 The tanks along the outside edge are countercurrent washing tanks 121. At the end of the countercurrent washing tanks are liquid-piston pumps 131. Fresh biomass 141 is pretreated and enters fermentor 111a the highest product concentration. When biomass is removed from fermentor 111a, it is washed in countercurrent washing tank 121a to remove product and passed on to the next fermentor 111b. In FIG. 3, the biomass flow is clockwise. Eventually, as it makes its way through all the fermentors, the biomass becomes digested. Fresh water 151, used to wash the spent solids, flows counterclockwise through the countercurrent washing tanks 121 until it is finally collected as concentrated product 161. In addition, liquid 171 is decanted from the top of one fermentor and pumped to the adjacent fermentor to increase the acid concentration. In an alternative embodiment, the liquid exiting the countercurrent wash tank could be directed to an adjacent fermentor, rather than to an adjacent countercurrent wash tank. In this case, the wash water fed to the countercurrent wash tank would be taken from an adjacent fermentor, rather than from an adjacent wash tank.

Figure 4:
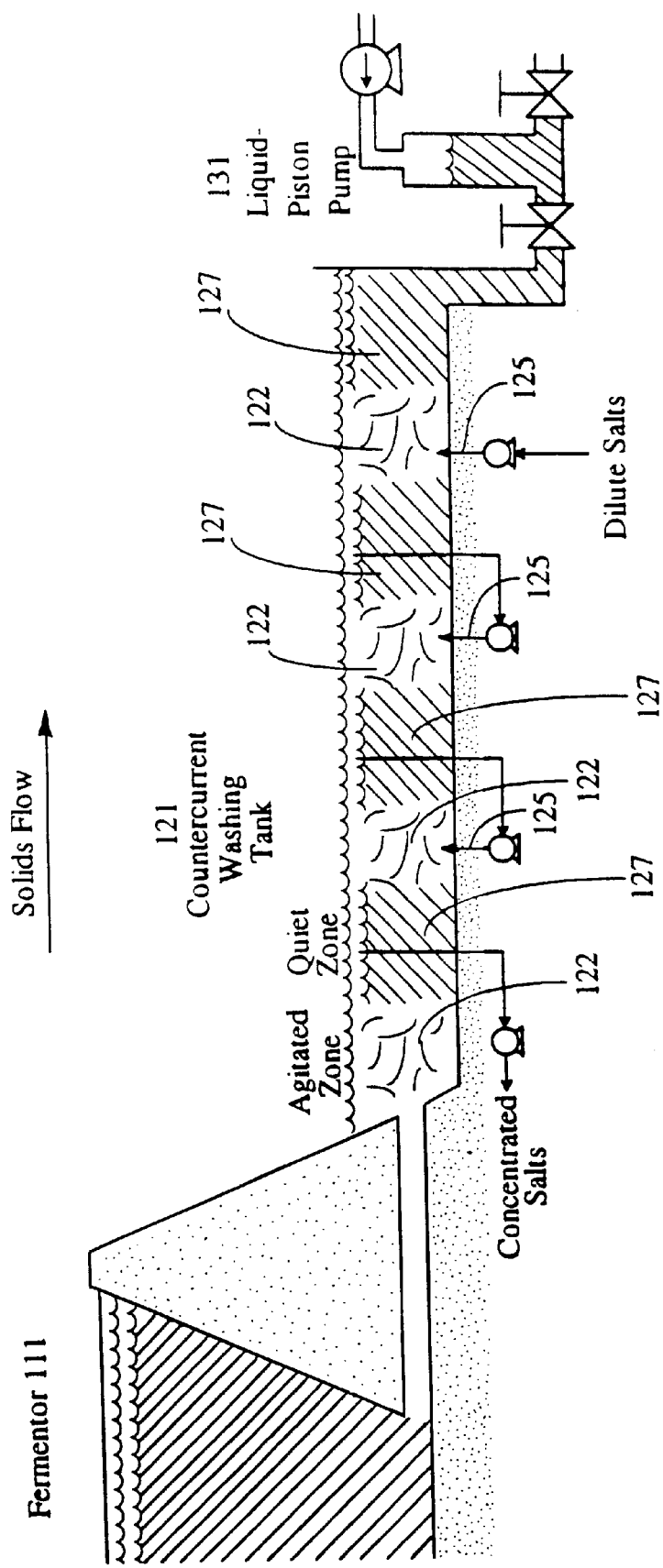
FIG. 4 shows a side view of a single biomass fermentor with associated countercurrent wash tank and liquid-piston pump.
Figure 5A:
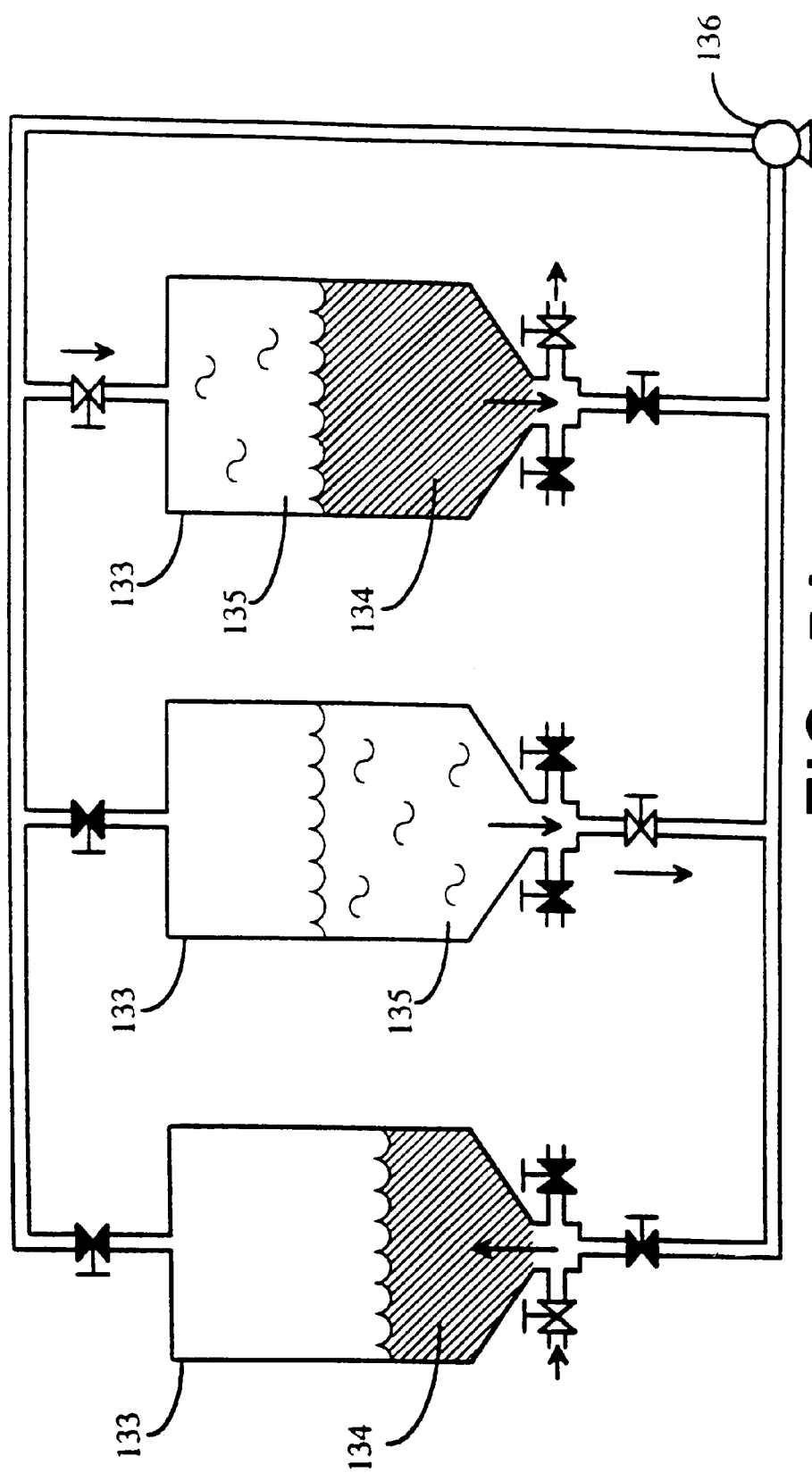
FIG. 5, subparts 1–6 show cycling of the liquid-piston pump.
Figure 5B:
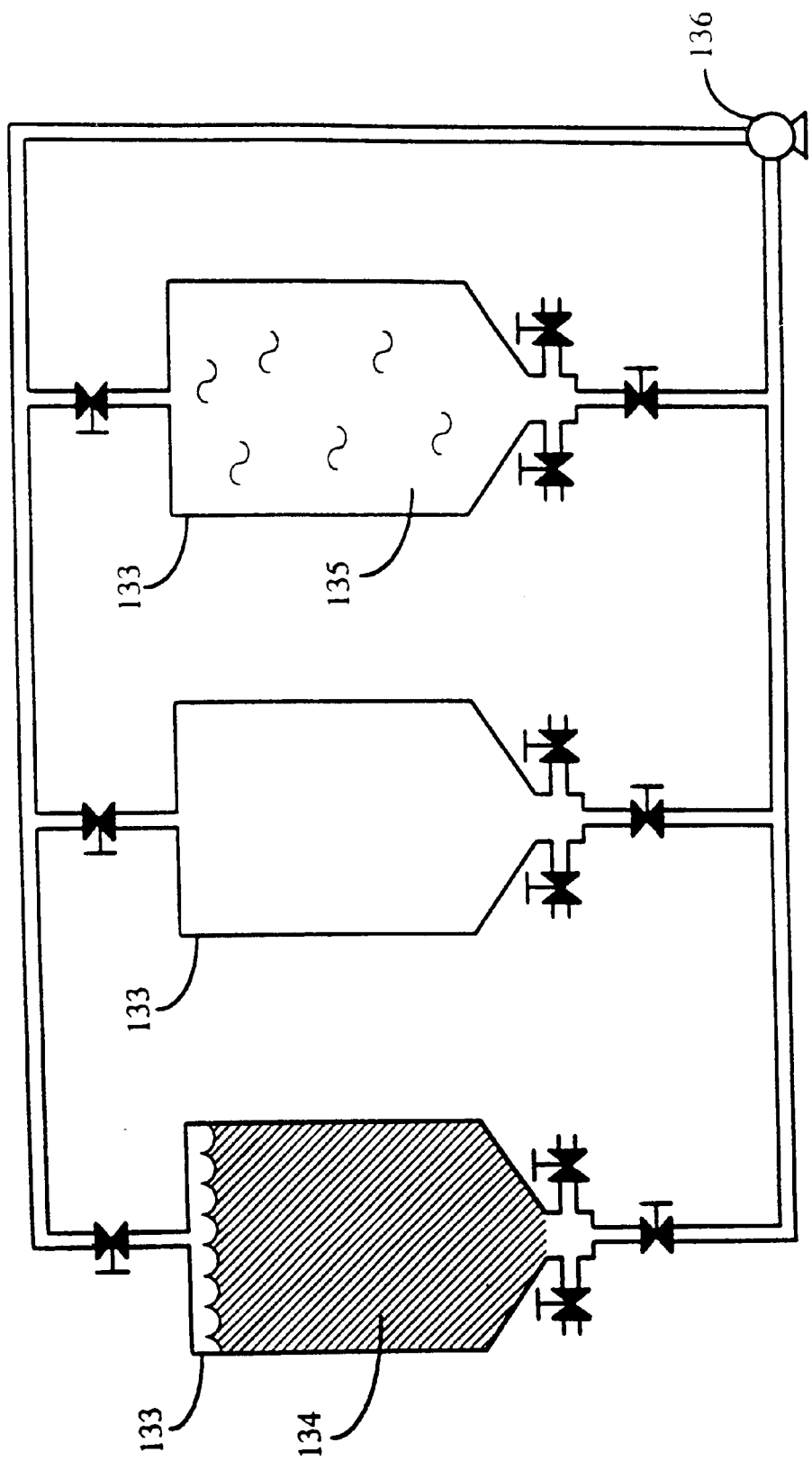
Figure 5C:
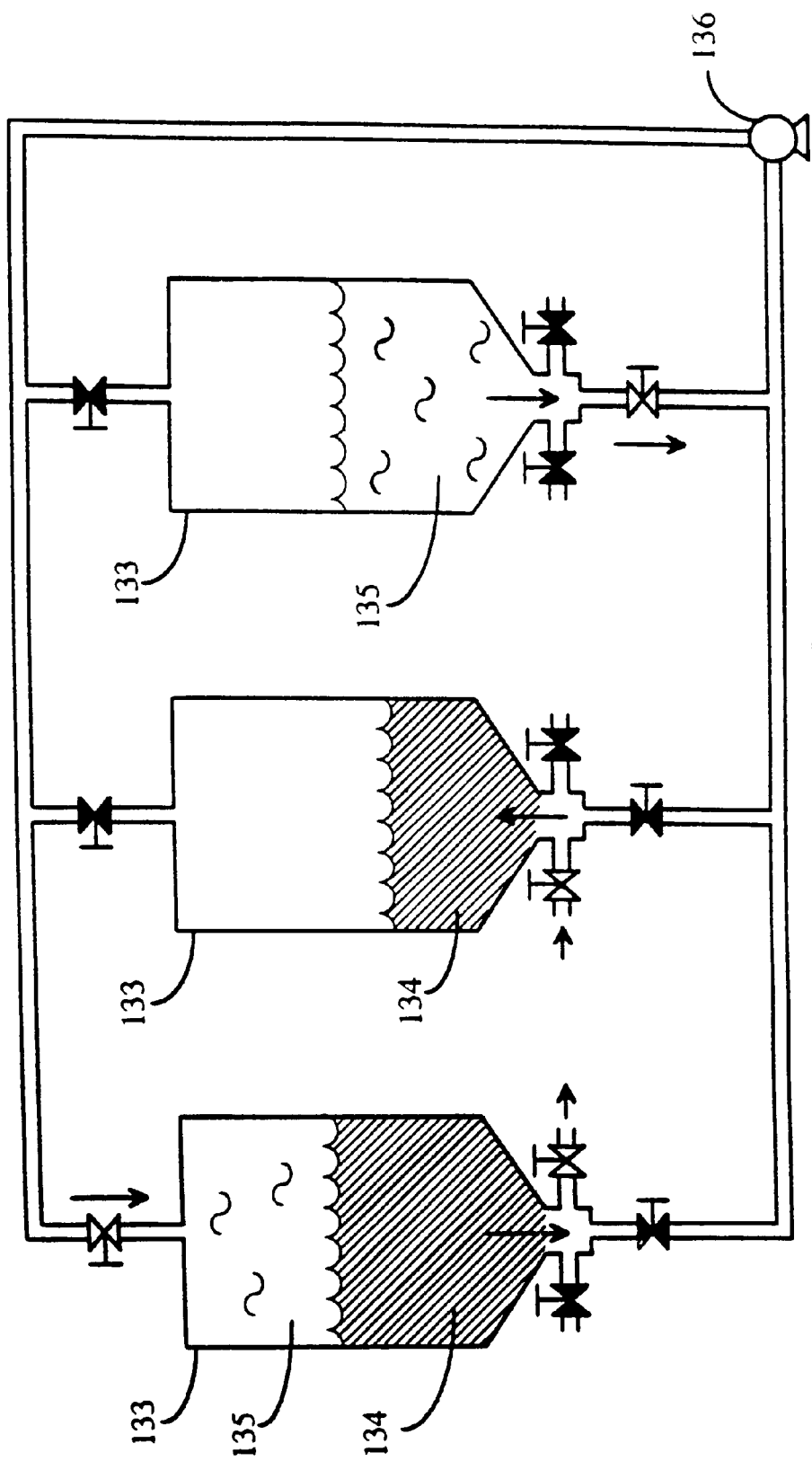
Figure 5D:
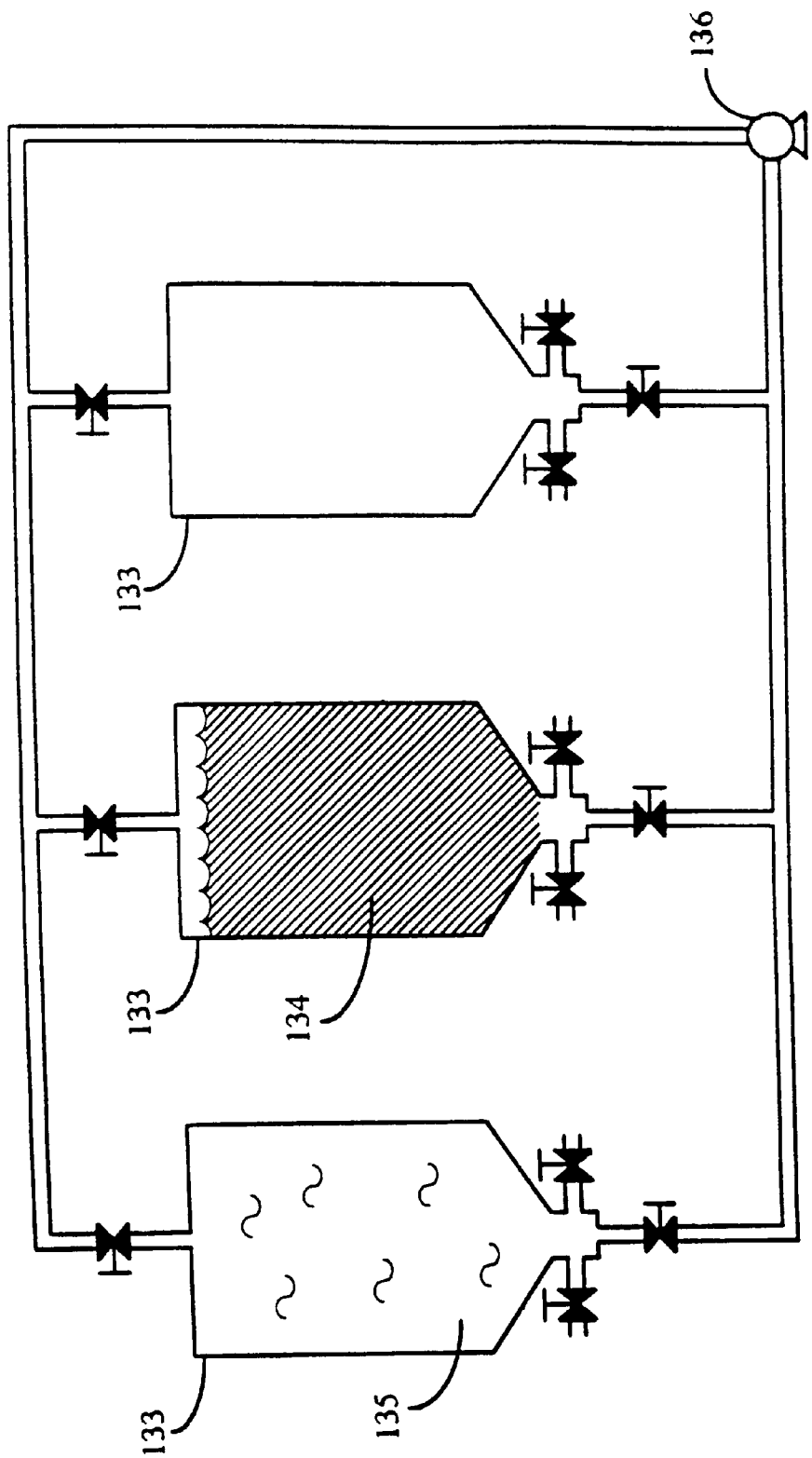
Figure 5E:
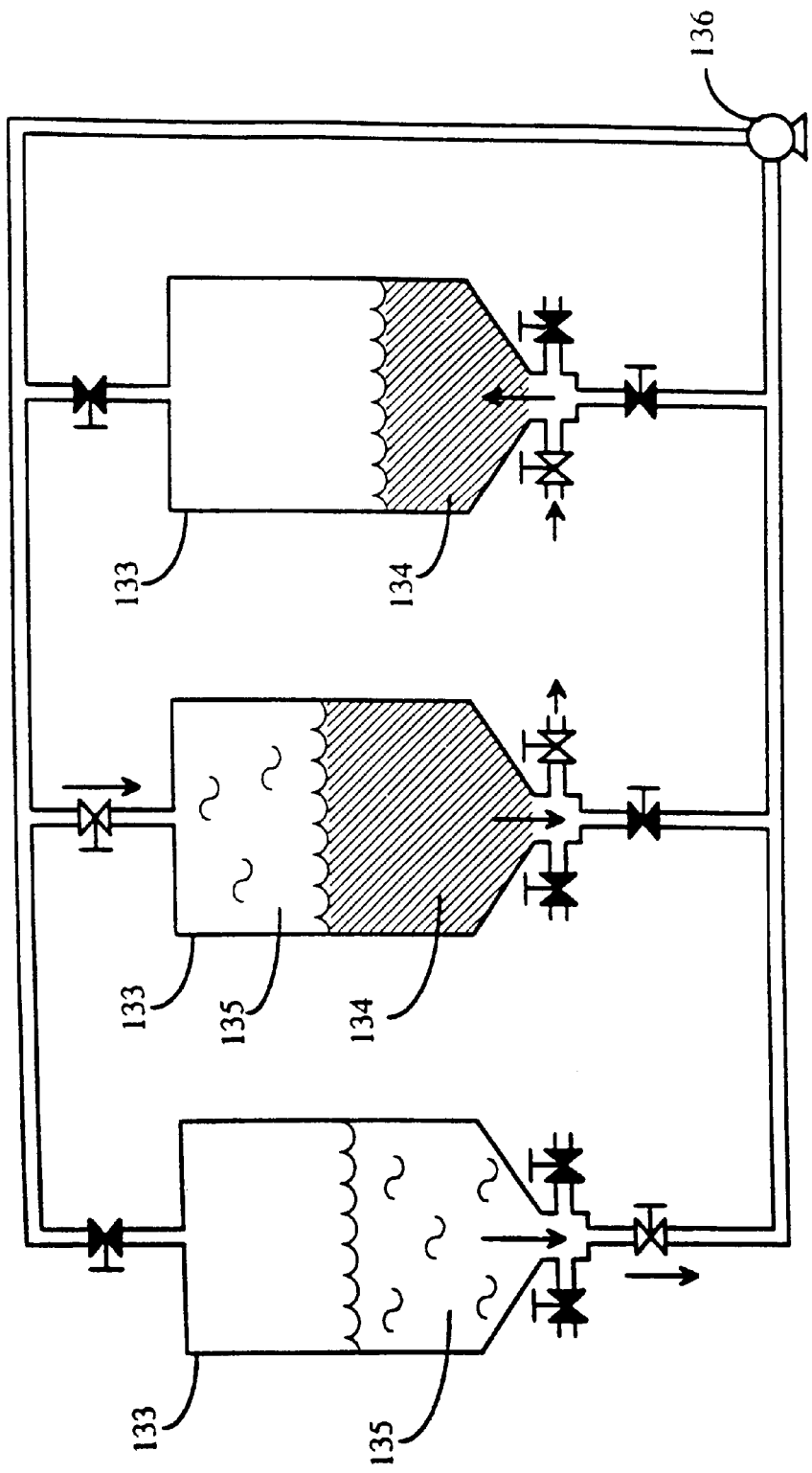
Figure 5F:
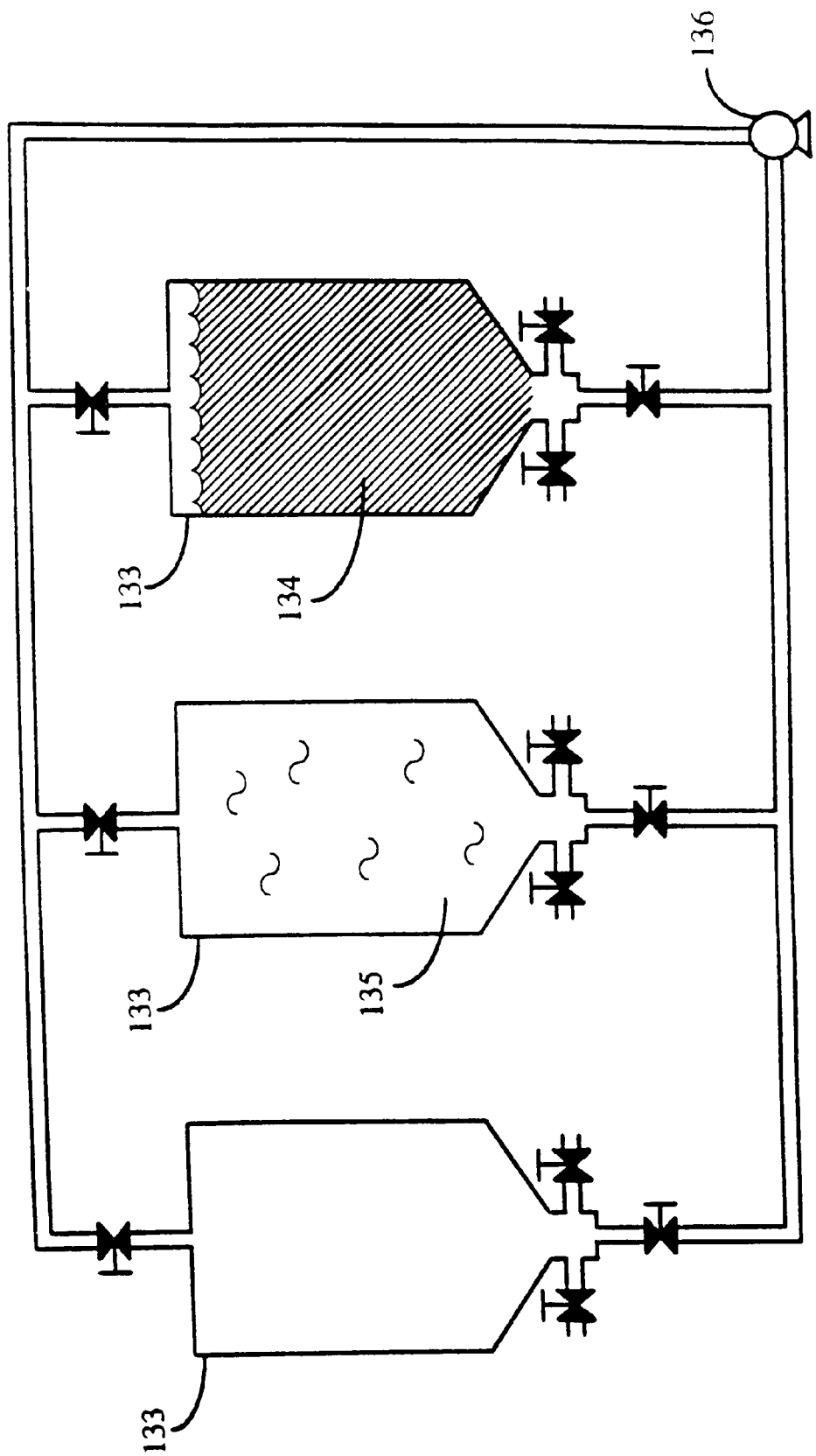

FIG. 4 shows a side view of a fermentor 111, a countercurrent washing tank 121, and a liquid-piston pump 131. The countercurrent washing tank consists of a series of agitated zones 122 and quiet zones 127. The agitation is achieved by an upward flow of liquid 125. The solids flow in one direction and the liquid flows in the other. At the end of the countercurrent wash tank is a liquid-piston pump 131. The liquid-piston pump is a set of three tanks (see FIG. which shows the set of three tanks at successive time points). At any given time, one tank is being filled (by gravity) with slurry 134, one is partially filled with liquid 135, and the other is being drained of slurry 134 by pumping liquid 135 into the top using liquid pump 136. When the cycle is complete, the function of each tank rotates. The primary advantage of this system is that solids-transfer pumps are not required to transport solids between fermentors; thus, an inexpensive method of achieving countercurrent flow has been provided.

Each fermentor 111 requires a countercurrent wash tank 121. The solids will occupy about two thirds of the tank with the remaining third wash water. Preferred tank configuration is the frustum of a rectangular pyramid. A single washing stage typically requires the replacement of the water within the solids with an equal volume of "new" water. Preferably, there are three washing stages per fermentor except for the last fermentor that has ten stages to get the last traces of acid out and each stage requires a solids washing pump, for a total quantity of 19 (3×3+10) pumps. However, these are all clear liquid pumps rather than the more expensive slurry pumps.

Figure 6:
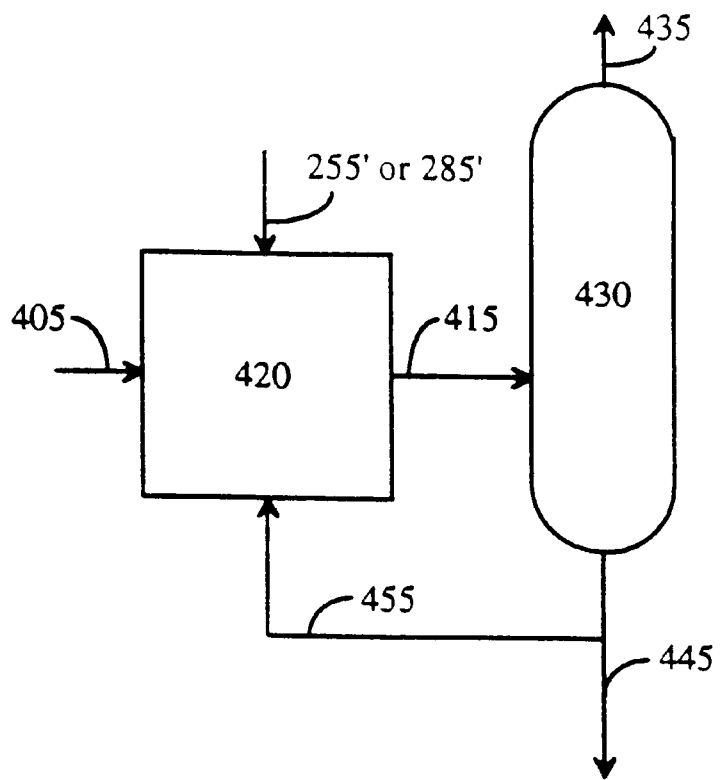
FIG. 6 shows a schematic representation of a fermentor and associated distillation column. (Fermentation Method F-B)

FIG. 6 shows an alternative Fermentation Method (F-B) in which both acetic acid and ethanol may be produced simultaneously by thermophilic bacteria. The cellulytic organism *Clostridium thermocellum* has a high cellulase activity and can convert hexoses into ethanol and acetic acid in approximately equal amounts. Because this organism is unable to utilize pentose sugars, *Clostridium thermosaccharolyticum, C. thermohydrosulfuricum*, or *Thermoanaerobacter ethanolicus* should be cocultured with the *C. thermocellum*. Biomass 405 is fed to fermentor 420 producing aqueous stream 415 containing approximately equal amounts of ethanol and acetic acid. Ethanol 435 may be recovered in distillation column 430, whereas acetic acid 445 would be concentrated and recovered by the method of this invention. If the organisms are more tolerant of acetate ions than ethanol some of distillation column bottoms 455 can be recycled to the fermentor allowing the acids to build to higher concentrations. Lime 285' or calcium carbonate 255' is added to the fermentor to maintain the pH near neutrality.

This process requires asepsis because a pure culture (or co-culture) is being maintained. For some systems, the lime treatment may be sufficient to sterilize both the biomass and water. However, if contamination is a problem, it is possible to sterilize the biomass by direct steam injection. The water can be sterilized using conventional sterilization equipment (i.e. countercurrent heat exchangers with a high-temperature holding section). The fermentor may be operated in either a batch or continuous mode, but the batch mode is likely to have fewer contamination problems.

Figure 7:
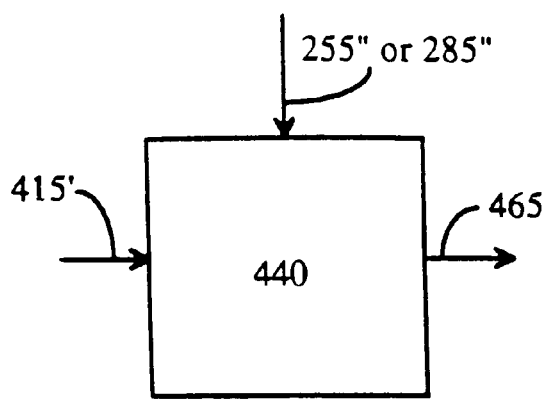
FIG. 7 shows a schematic representation of a fermentor for Fermentation Method F-C.

FIG. 7 shows yet another alternative Fermentation Method (F-C) in which an aqueous stream containing lactic acid 465 may be produced from a variety of sugars (e.g., lactose from whey, sucrose from sugar cane or sugar beets, glucose from starch hydrolyzates, pentoses from sulfite liquors, mixed sugars from cellulose hydrolyzates) in aqueous solution 415'. The organisms capable of performing the fermentation are generally drawn from the genera *Lactobacillus, Streptococcus, Pediococcus*, and *Rhizopus*. As the acid is produced in fermentor 440, lime 285" or calcium carbonate 255" is added to maintain a 5–7 pH.

Concentration

A key feature common to the family of processes is the concentration section of the plant where nonvolatile fermentation products (e.g., calcium acetate) are separated from water. Fermentation products are present in dilute aqueous solutions. Generally, there are about 30 kg of water per kg of product. This large amount of water must be removed to recover and purify the fermentation products. The VFA salt concentration exiting the fermentor is approximately 25 to 45 g/L, or approximately 25 to 40 parts of water per part of VFA salt. The $pK_a$ of VFAs is about 4.8 so at the fermentation pH (~5.8), only about 10% of the VFA is present as free unionized acid; the rest is ionic salt. Process steps that may be considered for concentrating the VFAs (or separating them from the water in the fermentation medium), include distillation, multiple-effect evaporation, vapor compression, heat pumps, reverse osmosis, and extraction of the VFAs from the water.

Distillation is only useful if the product is more volatile than the solvent. For nonvolatile products in aqueous fermentation medium, the water will go to the top of the distillation column and require enormous amounts of latent heat to vaporize the water. Both the salt and free unionized acid are less volatile than water, so distillation is not a preferred separation technique.

Multiple-effect evaporation techniques generally couple evaporators together. Heat (generally from process steam) is put into the first effect which vaporizes water. The water vapors produced from the first effect are thermally contacted with liquid at lower pressure in the second effect. When the vapors condense, they cause an equal amount of water to evaporate from the second effect. These water vapors, in turn, are contacted with the third effect which vaporizes more water, etc. Final-effect vapors are condensed by rejecting the heat to cooling water. Only the first effect requires heat input from process steam, yet the same amount of water is produced in each effect. Considering that there are about 30 kg of water per 1 kg of fermentation product, a four-effect evaporator would require that 7.5 kg of water be evaporated in the first effect. Even the energy cost of evaporating one-quarter of the water (i.e., in a quadruple effect evaporator) may be too expensive in many modes of operation, because it represents about 10% of the selling price of many of these fermentation products.

Vapor compression is performed using a compressor to pull a vacuum on the fermentation liquid causing it to boil. These low-pressure vapors are then compressed to a slightly higher pressure. These higher-pressure vapors are in thermal contact with the liquid. When they condense, they supply the latent heat necessary to evaporate more water from the fermentation liquid. Only a single heat exchanger is required to transfer heat from the condensing vapors to the boiling liquid. This approach requires very large compressors, because the specific volume of water vapors is so large. Also, high quality energy in the form of work (e.g., electricity, shaft work) must be supplied, so this is expensive.

Heat pumps are similar to the vapor compression approach, except an alternate fluid (e.g., ammonia, Freon) is compressed rather than water. A smaller compressor may be used, because these alternate fluids have a much lower specific volume than low-pressure steam. Unfortunately, this method requires two heat exchangers (e.g., condensing-ammonia-to-boiling-fermentation-liquid and boiling-ammonia-to-condensing-water-vapor), so the irreversibilities, associated with transferring heat are usually too great. This approach also requires high quality energy in the form of work.

Membrane techniques (e.g., reverse osmosis, electrodialysis, water-splitting electrodialysis, carrier-mediated transport membranes) may also be considered, but the cost of membranes makes this prohibitive. In reverse osmosis, the fermentation liquid is pumped to about 55 atm and contacted with a membrane that selectively passes water, but rejects salt ions. Because the salt ions are retained behind the membrane, they become concentrated. This method uses high quality energy in the form of work (e.g., electricity or shaft work). The membranes foul easily and must be replaced approximately every two years. Also, there are few economies of scale associated with membrane processes, because the membrane area increases linearly with plant capacity.

Playne (in Moo-Young et al., eds., "Comprehensive Biochemistry," Pergamon Press, New York, 1985, Vol. 3, pp. 731–759) discusses many techniques for recovering VFAs from dilute aqueous solutions. Some proposed methods employ immiscible solvents (e.g., tributyl phosphate, trioctyl phosphine oxide, high-molecular-weight amines) that react with the free unionized acid and extract it from the broth. For solvent extraction to be effective, the fermentor pH must be acidic (4.8 to 5.2) which severely inhibits the microorganisms. Alternatively, if the fermentation is operated near neutrality, the fermentation broth can be acidified with mineral acids (which generates wastes) or carbon dioxide (which requires high pressures).

One approach to extracting fermentation product from the water is described in U.S. Pat. No. 4,444,881. The calcium salt (e.g., calcium acetate) in the fermentation broth is contacted with a tertiary amine (e.g., tributylamine) and carbon dioxide. Insoluble calcium carbonate precipitates leaving the tributylamine acetate in solution which is then extracted using a suitable solvent (e.g., chloroform). The chloroform is then evaporated away from the tributylamine acetate. Upon heating, the tributylamine acetate decomposes into tributylamine (which is recycled) and acetic acid. Tertiary amines are preferred over primary or secondary amines because the latter tend to form amides upon heating which represents a loss of product. Extraction of the tributylamine acetate from the liquid must be very complete because the water will be recycled to the fermentor. Unrecovered tributylamine will be consumed by the fermenting organisms and lost. This loss could be reduced by adsorbing the residual tributylamine acetate on activated carbon, but this requires an additional costly step. The precipitated calcium carbonate must be thoroughly washed to recover all tributylamine. Enormous amounts of solvent (e.g., chloroform) must be evaporated. The distribution coefficient is apparently less than one, so the tributylamine acetate which was in water is now present in an even greater amount of solvent. Salts (e.g., potassium phosphorous) present in the feedstock biomass have no way to leave the fermentation system. They will accumulate to inhibitory levels, so a purge stream will be required.

Rather than extracting salts from the water, the water may be extracted from the salt using secondary or tertiary amines with five to six carbon atoms per molecule. Prior to extraction, the fermentation broth is first contacted with lime to raise the pH to about 11.5. At this pH, minerals precipitate as well as carbohydrate polymers. The precipitate is removed (e.g., by settling) so it does not interfere with the water extraction process.

The amine dewatering system of this invention (see, e.g., FIG. 1) exploits interesting properties of low-molecular-weight secondary and tertiary amines. The amines are substantially immiscible in water. At low temperatures (e.g., 40° C.), water is highly soluble in the amine, but when the temperature is raised by about 20° C. (e.g., to 60° C.), water becomes substantially insoluble in the amine. By contacting a water-lean amine with fermentation broth, water is selectively absorbed leaving the salt behind. Using countercurrent contacting, with sufficient quantities of amine (approximately five times as much amine as fermentation broth), enough water can be extracted to increase the salt concentration in the fermentation broth from about 25 to 45 g/L (i.e. 2.5 to 4.5%) to about 200 g/L (i.e. 20%). The water-rich amine that contains the extracted fermentation water is then heated in a countercurrent heat exchanger and is sent to a separator in which steam is injected to raise the temperature by about 20° C.–25° C.

This causes water to phase out of the amine which then is decanted. Latent heat is required to cause the phase separation of water-and amine. Because the temperature in the separator is relatively low (e.g., 60° C.), it provides a convenient place to usefully reject waste heat from other sections of the plant.

Water extraction using amines was explored in the 1950's and 1960's as a method for water desalination. Although reverse osmosis is the current preferred method for water desalination, extracting water from the fermentation liquid appears preferable for concentrating fermentation broths. Extraction will scale approximately with the 0.6 power of capacity whereas reverse osmosis scales almost linearly. Therefore extraction will achieve economies of scale in large plants but reverse osmosis will not. Reverse osmosis is very sensitive to membrane fouling whereas extraction is not. It will be difficult to separate all the solids (e.g., lignin, cells) to meet the cleanliness requirements of reverse osmosis. To produce drinking water with a low salt content, the extraction process needed a reflux stream of water, so both a stripper section and a rectifier section were included in the extraction column. However, recovering salts from fermentation broths does not need a rectifier section because any salts in the extracted water are simply recycled to the fermentors.

Because the extraction amines are not completely immiscible, they are present in the product water at about a 5% concentration. These amines must be removed by stripping. The stripping efficiency is low at neutral or acidic pH (where the amine is an ionized salt) and high at alkaline pH (where the amine is not ionized). It was not possible to adjust the pH to sufficiently alkane conditions when making drinking water, but it is entirely possible in recovery of biomass fermentation products. This amine dewatering process is described in greater detail in application Ser. No. 08/885,841, filed concurrently herewith entitled "Recovery of Fermentation Salts from Dilute Aqueous Solutions," and incorporated herein by reference in its entirety.

Recovery/Conversion

The salts of VFAs are optionally precipitated from the concentrate obtained from the fermentation liquor and dried. Recovery of desired product from the concentrate or dry salt can be by any one of the following processes.

In a particular embodiment (Recovery Method R-A), the products are low-molecular weight ketones produced by a process that thermally converts salts of volatile fatty acids (VFAs) into ketones in good yield. In the metal salts of VFAs, the anion portion of the salt is provided by the VFAs, whereas the cations are usually alkali or alkaline earth metal cations. Preferred salts include, e.g., lithium, sodium, potassium, magnesium, calcium or barium salts, or a mixture of two or more of these salts.

Figure 8:
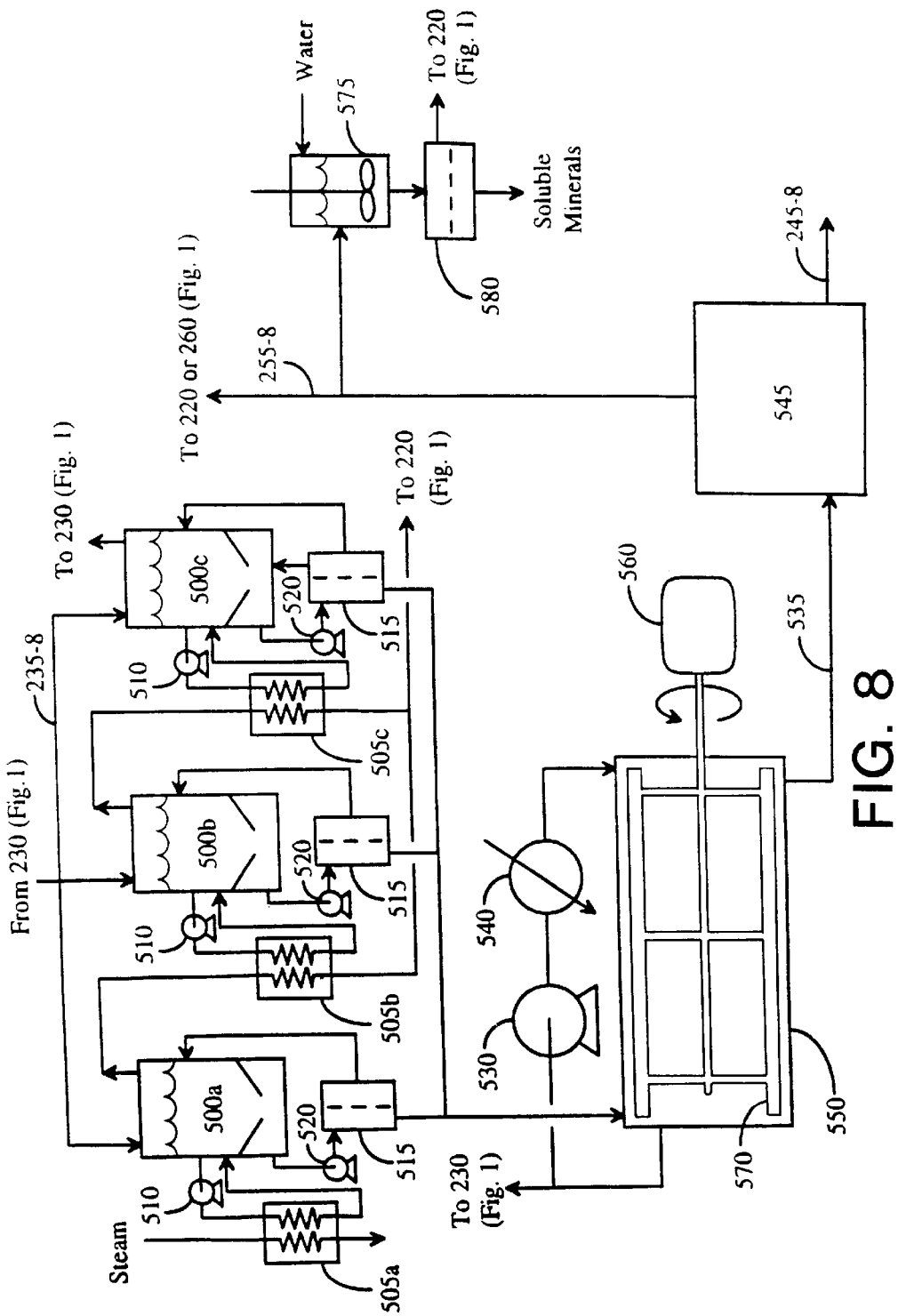
FIG. 8 shows a schematic representation of Recovery Method R-A.

FIG. 8 shows a schematic representation of Recovery Method R-A. VFA salts 235-8 from a dewatering system (e.g., amine dewatering system 230 in FIG. 1) should have a concentration of approximately 20%. The pH of the concentrated salt solution from the amine dewatering system is alkaline. To avoid undesirable reactions in thermal convertor 545, the pH can be adjusted downward by adding carbon dioxide. These acid salts enter a multiple-effect evaporator which consists of vapor disentrainers 500, heat exchangers 505, and circulating pumps 510. Three effects are indicated in FIG. 8, but fewer or more may be used depending upon economic considerations. The vapor disentrainers operate at successively lower pressures with vapor disentrainer 500a operating at the highest pressure and vapor disentrainer 500c operating at the lowest pressure. Process steam is fed to heat exchanger 505a which produces vapors which are disentrained in vapor disentrainer 500a. The vapors disentrained in vapor disentrainer 500a are fed to heat exchanger 505b which produces vapors that are disentrained in vapor disentrainer 500b. This process is repeated in subsequent effects. The vapors generated in the lowest pressure effect (vapor disentrainer 500c) are directed to an earlier stage in the process (e.g., amine dewatering system 230 in FIG. 1) to provide the latent heat needed to separate water from amine.

The vapor disentrainers 500 are partitioned into two zones, one agitated (shown at the top in FIG. 8) and the other quiescent. Liquid from the agitated zone is circulated through the heat exchanger and is returned to the agitated zone. As vapors are removed, salt precipitates and settles into the quiescent zone. The suspended precipitate in the quiescent zone is pumped through solids separator 515 (e.g., filter, cyclone, or centrifuge) and the solid-free liquid is returned to the agitated zone of the vapor disentrainer.

The salts recovered from the solids separator 515 are sent to drier 550 which is agitated by impellor 570 driven by motor 560. The saturated water vapor from drier 550 is propelled by blower 530 through heat exchanger 540 which superheats the vapors. The superheated vapor is returned to drier 550 where the sensible heat provides the latent heat necessary for water to vaporize from the wet salt. Most of the water vapor is circulated through drier 550 whereas a small portion, that which is vaporized from the wet salt, is removed from drier 550 and sent to an amine dewatering system to provide the latent heat needed to separate water from amine.

The dry salt 535 enters the thermal convertor 545 which is described in greater detail in application Ser. No. 08/885,774, entitled "Thermal Conversion of Volatile Fatty Acids to Ketones," filed concurrently herewith and incorporated herein by reference in its entirety. The ketones 245-8 are recovered as product or sent to a hydrogenator for conversion to secondary alcohols. Stream 255-8 contains mainly calcium carbonate but may also contain soluble minerals that may be purged from the system by drawing a side stream, dissolving a portion of it in water using mixer 575, and removing the insoluble calcium carbonate using solids separator 580 (e.g., filter, cyclone, or centrifuge). The soluble minerals will be in the water and may be purged from the system. The majority of stream 255-8 will be sent to either the lime kiln or directly to the fermentor in the process shown in FIG. 1.

In an alternative embodiment, the process according to this invention can be used to produce aldehydes by including calcium formate (or another metal formate salt) with the VFA salts introduced into the reaction chamber. This will usually produce mixed aldehyde/ketone product which can be separately by distillation. Alternatively, the mixed aldehyde/ketone product can be hydrogenated to produce mixed primary and secondary alcohols.

Hydrogenation

It is possible that the ketones may be inexpensive enough for use as motor fuel. Because ketones are not currently accepted for blending in fuel they should be hydrogenated first. This is easily accomplished at room temperature and room pressure by contacting the ketone with hydrogen gas using a Raney nickel catalyst. The reaction proceeds more rapidly at higher temperatures, but the equilibrium becomes less favorable.

The liquid ketone product can be converted to alcohols by hydrogenation. From typical VFA compositions in the fermentor, four ketones (2-propanone (acetone), 2-butanone, 2-pentanone, and 3-pentanone) comprise about 900% of the expected product. The hydrogenation may be performed at 1 atm total pressure and near-ambient temperature using Raney nickel catalyst. Comparing the hydrogenation rates of the four ketones at 40° C., they are all very similar and differ at most by a factor of two. The reaction rate increases linearly with hydrogen pressure and catalyst concentration provided the reactor is not mass transfer limited.

The hydrogen would likely be derived from reformed natural gas, an abundant domestic energy source. In large-scale production, hydrogen costs about the same as gasoline per unit of energy, so there are no economic penalties associated with its use. The ketone may be viewed as a hydrogen carrier which avoids the need for high-pressure tanks to store gaseous hydrogen in automobiles.

Acid Recovery

Figure 9:
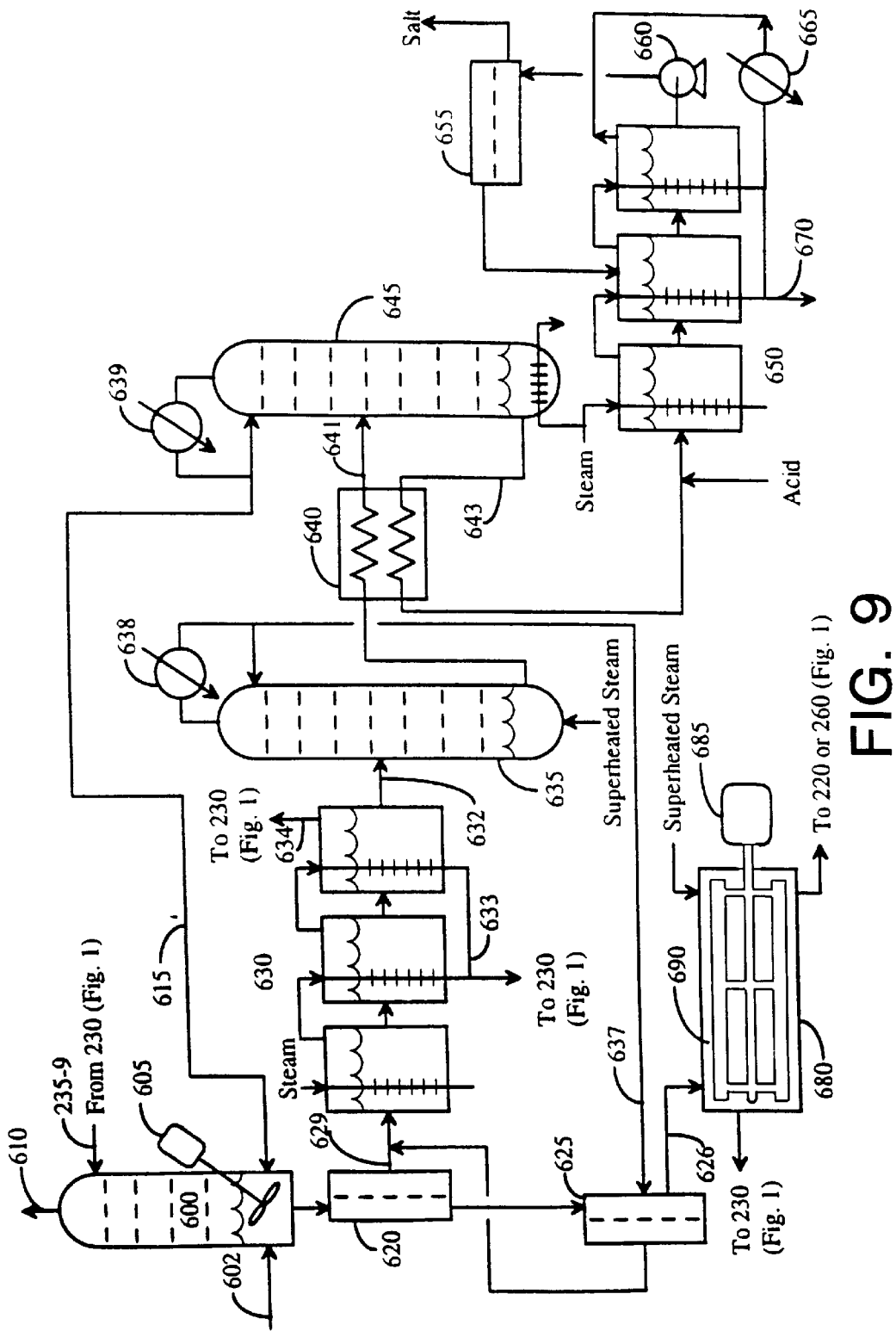
FIG. 9 shows a schematic representation of Recovery Method R-B.

FIG. 9 shows a schematic representation of Recovery Method R-B which allows high-boiling acids (e.g., lactic acid) to be "sprung" from calcium salts of acids. An acid salt solution 235-9 such as that from the amine dewatering section 230 in FIG. 1, which is about 20% acid salt with the remainder water, flows into contactor 600 which contacts the acid salt solution with a carbon-dioxide-rich stream 602 and a low-molecular-weight tertiary amine 615, preferably the same amine used in amine dewatering system 230 (see FIG. 1). A lower water content is possible if the acid salt solution is additionally dewatered using multiple-effect evaporators. The low-molecular-weight tertiary amine 615, acid salt solution 235-9, and carbon-dioxide-rich gas 602 are agitated by mixer 605 to ensure good contact of all species. A reaction occurs in which the calcium in stream 235-9 reacts with the carbon dioxide in stream 602 and precipitates as calcium carbonate allowing the amine to form an amine/acid complex.

To ensure that little of the volatile, low-molecular-weight tertiary amine leaves the contactor 600, contacting trays may be placed above the mixer. Exhaust gas exits in stream 610.

The calcium carbonate precipitate is removed in solids separator 620 (e.g., filter, cyclone, or centrifuge). Using solids separator 625, wash water 637 removes residual amine/acid complex. Optionally, solids separator 620 and 625 may be the same piece of equipment; for ease of understanding, the filtration modes and washing operating modes are shown in FIG. 9 using different pieces of equipment. Washed calcium carbonate 626 may be sent to the fermentor (e.g., 220 in FIG. 1) or a lime kiln (e.g., 260 in FIG. 1) provided the amine content is low enough. If necessary, the volatile amine can be removed from the calcium carbonate using drier 680. Motor 685 rotates the impellor 690 to ensure good contact between the superheated steam and the solid calcium carbonate. The exiting steam may be sent to the amine dewatering system (e.g., 230 in FIG. 1) to provide energy to phase water out of the amine.

If the above reaction is performed with a large amount of water, the water may be removed from stream 629 using multiple-effect evaporator 630. Three effects are shown in FIG. 9, but fewer or more may be employed depending upon economic concerns. Any amine in streams 633 and 634 may be separated from the water by stripping. Alternatively, to promote energy efficiency, streams 633 and 634 may be returned to the amine dewatering system (e.g., 230 in FIG. 1), provided the same amine is used in both systems. The vapors exiting the multiple-effect evaporator 634 can be used to supply the latent heat needed for phase separation of the water and amine in the amine dewatering system (e.g., 230 in FIG. 1).

Liquid stream 632 exiting multiple-effect evaporator 630, may contain small amounts of water that may be removed in distillation column 635. Distillation column 635 is operated below the temperature at which the amine/acid complex decomposes. Superheated steam (or an inert gas) is added at the bottom of the column to promote good mass transfer on the trays. By drawing a side stream of liquid from trays on the column (not shown in FIG. 9), and supplying heat using a heat exchanger, water will evaporate leaving the amine/acid complex primarily in the liquid phase. Condenser 638 allows reflux to be added to the distillation column to ensure little amine exits the top. To promote energy efficiency, the latent heat from condenser 638 may be rejected to the amine dewatering system (e.g., 230 in FIG. 1). Distillation column 635 can be eliminated if water can be tolerated in the downstream processing steps.

The bottoms from distillation column 635 are preheated in countercurrent heat exchanger 640 and are introduced to reactive distillation column 645. This column is operated above the decomposition temperature of the amine/acid where the following reaction occurs

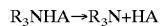

The volatile low-molecular-weight tertiary amine exits the top of the column. Condenser 639 20 allows reflux to be added to the distillation column to ensure little acid exits the top. To promote energy efficiency, the latent heat from condenser 639 may be rejected to the amine dewatering system (e.g., 230 in FIG. 1). The condensed amine is recycled to contactor 600.

Acid 643 exiting the bottom of reactive distillation column 645 is cooled in countercurrent heat exchanger 640 and sent to multiple-effect evaporator 650 to remove residual salts from product acid 670. Condenser 665 condenses vapors from the lowest pressure effect. To. promote energy efficiency, the latent heat may be rejected to the amine dewatering system (e.g., 230 in FIG. 1). Depending upon the acid, it may be necessary to operate multiple-effect evaporator 650 under vacuum to prevent thermal decomposition. By pumping the acid/salt slurry using pump 660, residual salts are separated using solids separator 655. If necessary, a small amount of acid (e.g., sulfuric acid) can be added to ensure that all salt cations (e.g., K+) have an accompanying anion (e.g., $SO_4^{2-}$).

Because of its relative simplicity, Recovery Method R-B is a preferred method provided the boiling point of the acid is above the thermal decomposition temperature of the amine/acid complex. By altering the pressure in reactive distillation column 645, it is possible to adjust the boiling point and decomposition temperature.

Figure 10:
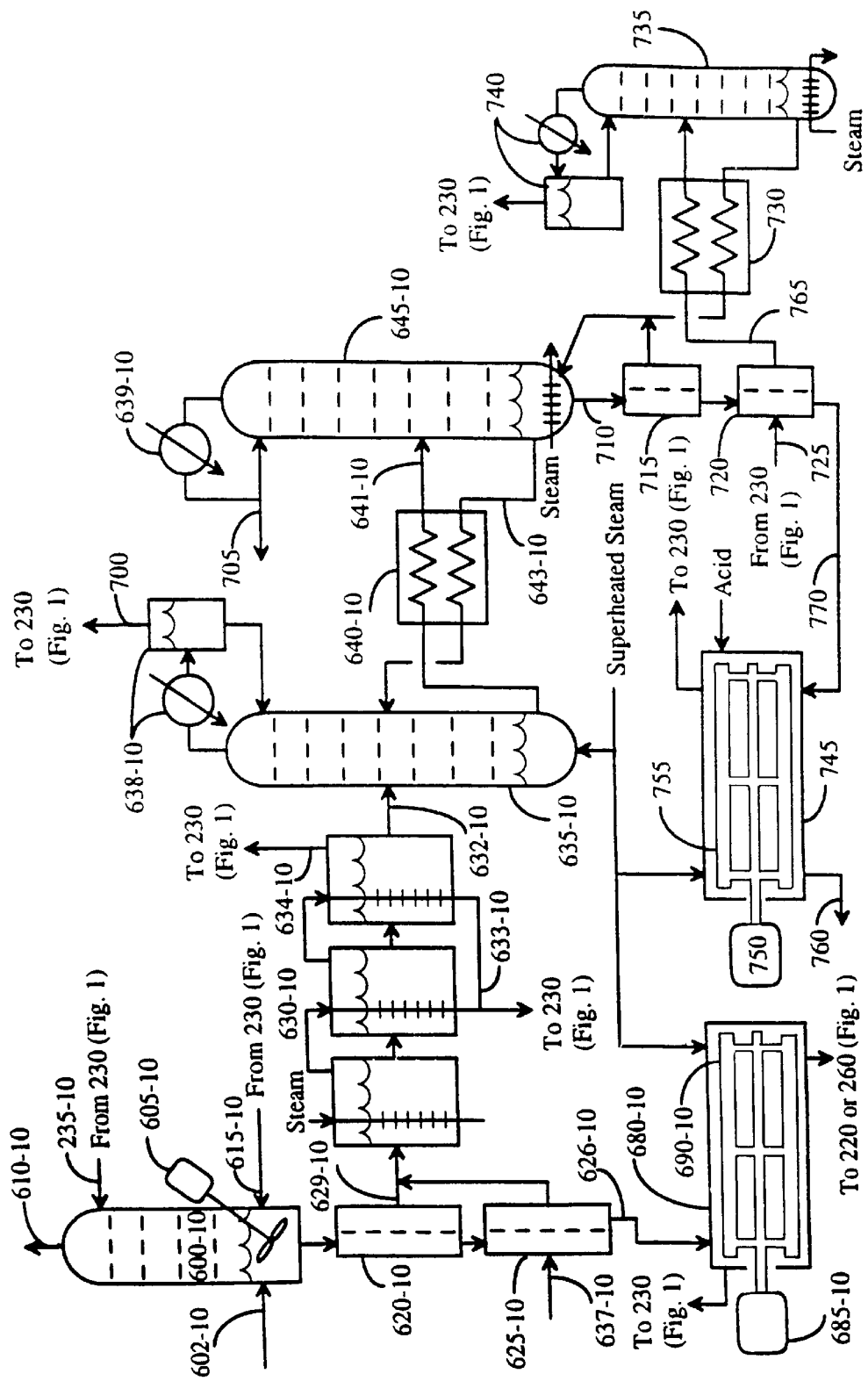
FIG. 10 shows a schematic representation of Recovery Method R-C.

An alternative embodiment is shown in FIG. 10 (Recovery Method R-C) which allows low-boiling acids (e.g., acetic) to be "sprung" from calcium salts of acids. Acid salt solution 235-10 from the amine dewatering section (e.g., 230 in FIG. 1) is preferably about 20% acid salt with the remainder water. A lower water content is possible if the acid salt solution is additionally dewatered using multiple-effect evaporators. Acid salt solution 235-10 flows into contactor 600-10 which contacts the acid salt solution with carbon-dioxide-rich stream 602-10 and low-molecular-weight tertiary amine 615-10, preferably the same amine used in the amine dewatering system (e.g., 230 in FIG. 1). Low-molecular-weight tertiary amine 615-10, acid salt solution 235-10, and carbon-dioxide-rich gas 602-10 are agitated with mixer 605-10 to ensure good contact of all species. A reaction occurs in which the calcium in stream 235-10 reacts with the carbon dioxide in stream 602-10 and precipitates as calcium carbonate allowing the amine to form an amine/acid complex.

$$CaA_2 + CO_2 + 2R_3N + \rightarrow CaCO_3 + 2R_3NHA$$

To ensure that little of the volatile, low-molecular-weight tertiary amine leaves the contactor 600-10, contacting trays may be placed above the mixer. Exhaust gas exits stream 610-10. In a slight modification of this scheme, stream 235-10 would contain a significant amount (~5%) of amine if it were not stripped in the amine dewatering system (e.g. 230 in FIG. 1). In this case, the amine-laden feed would be added on a lower tray. To prevent amine from leaving in stream 610-10, a small side-stream would be pulled from stream 235-10, stripped of amine, and the resulting amine-free bottoms would be added on the top tray of contactor 600-10.

The calcium carbonate precipitate is removed in solids separator 620-10 (e.g., filter, cyclone, or centrifuge). Using solids separator 625-10, wash water 637-10 removes residual amine/acid complex. Solids separator 620-10 and 625-10 could be the same piece of equipment; for ease of understanding, the filtration modes and washing operating modes shown in FIG. 10 use different pieces of equipment. The washed calcium carbonate 626-10 may be sent to fermentor 220 or lime kiln 260 (see FIG. 1) provided the amine content is low enough. If necessary, the volatile amine can be removed from the calcium carbonate using drier 680-10. Motor 685-10 rotates the impellor 690-10 to ensure good contact between the superheated steam and the solids. The exiting steam is sent to the amine dewatering system (e.g., 230 in FIG. 1) to provide energy for water to phase out of the amine.

If the above reaction is performed with a large amount of water, the water may be removed from stream 629-10 using multiple-effect evaporator 630-10. Three effects are shown in FIG. 10, but fewer or more may be employed depending upon economic concerns. Any amine in streams 633-10 and 634-10 may be separated from the water by stripping. Alternatively, to promote energy efficiency, streams 633-10 and 634-10 may be returned to the amine dewatering system, provided the same amine is used in both systems. The vapors exiting the multiple-effect evaporator 634-10 can be used to supply the latent heat needed to phase separate the water and amine in the amine dewatering system.

Liquid stream 632-10 exiting the multiple-effect evaporator 630-10 contains low-molecular-weight tertiary amine/acid complex and small amounts of water. In the distillation column 635-10, the low-molecular-weight amine $R_3N$ is replaced with a high-molecular-weight amine $R'_3N$ $$R_3NHA + R'_3N \rightarrow R'_3NHA + R_3N$$

Suitable high-molecular-weight amines include higher alkanes (e.g., tributylamine, trioctylamine) and triethanol amine. Although triethanol amine itself does not have a high molecular weight, it reacts with the organic acids to make esters that do have very high molecular weights. Triethanol amine is preferred because it is inexpensive and widely used in natural gas processing.

The distillation column 635-10 is operated below the temperature at which the amine/acid complex decomposes (triethylamine acetate decomposes at 140° C. to 160° C.). Superheated steam (or an inert gas) is added at the bottom of the column to promote good mass transfer on the trays. By drawing a side stream of liquid from trays on the column (not shown in FIG. 10), and supplying heat using a heat exchanger, water and low-molecular-weight tertiary amine will evaporate leaving the high-molecular-weight tertiary amine/acid complex primarily in the liquid phase. A partial condenser 638-10 allows reflux to be added to the distillation column to ensure that little high-molecular-weight amine exits the top. To promote energy efficiency, the vapors 700 from the partial condenser may be directed to the amine dewatering system (e.g., 230 in FIG. 1).

The bottoms 641-10 from distillation column 635-10 contain high-molecular-weight tertiary amine/acid complex. They are preheated in countercurrent heat exchanger 640-10 and are introduced to reactive distillation column 645-10. This column is operated above the decomposition temperature of the amine/acid (approximately 170° C.) where the following reaction occurs $$R'_3NHA \rightarrow R'_3N + HA$$

Volatile acid 705 exits the top of the column. Condenser 639-10 allows reflux to be added to the distillation column to ensure little amine exits the top. To promote energy efficiency, the latent heat from condenser 639-10 may be rejected to the amine dewatering system (e.g., 230 in FIG. 1).

High-molecular-weight tertiary amine 643-10 exiting the bottom of reactive distillation column 645-10 is cooled in countercurrent heat exchanger 640-10 and sent to distillation column 635-10 to exchange with the low-molecular-weight tertiary amine.

A small stream 710 is withdrawn from the bottoms of reactive distillation column 645-10 to recover precipitated minerals that accumulate. Solids separator 715 (e.g., filter, hydroclone, centrifuge) removes the solids from the high-molecular-weight tertiary amine. These solids are sent to solids separator 720 where they are washed with low-molecular-weight tertiary amine 725. Solids separator 715 and 720 could be the same piece of equipment; for ease of understanding, the filtration modes and washing operating modes shown in FIG. 10 use different pieces of equipment. The liquid stream exiting solids separator 720 is a mixture of high-molecular-weight tertiary amine and low-molecular-weight tertiary amine. This stream is preheated using countercurrent heat exchanger 730 and sent to distillation column 735 which separates the two amines. Partial condenser 740 condenses some of the low-molecular-weight tertiary amine and refluxes it back to the distillation column to prevent high-molecular-weight tertiary amine from exiting the tops. The vapors exiting distillation column 735 are sent to the amine dewatering system (e.g., 230 in FIG. 1) to provide energy for phasing water out of the amine.

Washed solids 770 are directed to drier 745 where they are contacted with superheated steam that strips off residual low-molecular-weight tertiary amine. To ensure good contact of solids with the superheated steam, the contents are agitated using impellor 755 driven by motor 750. Dry minerals 760 exit drier 745. If necessary, a small amount of acid (e.g., sulfuric acid) can be added to ensure that all salt cations (e.g., $K^+$) have an accompanying anion (e.g., $SO_4^{2-}$).

Figure 11:
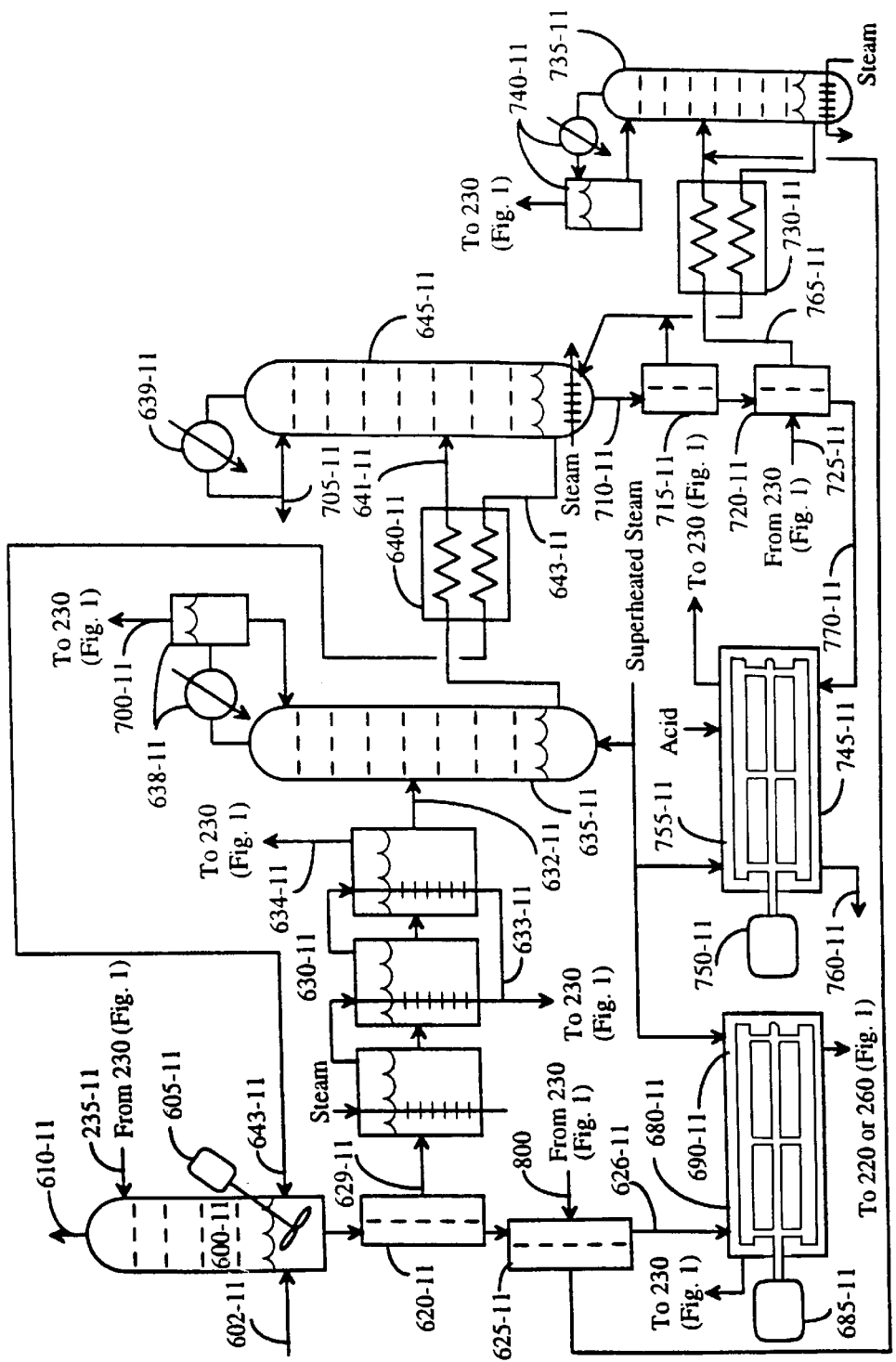
FIG. 11 shows a schematic representation of Recovery Method R-D.

Yet another embodiment is shown in FIG. 11 (Recovery Method R-D) which also allows low-boiling acids (e.g., acetic) to be "sprung" from calcium salts of acids. In this method, the calcium salts of the acid are directly contacted with high-molecular-weight tertiary amine, unlike the previous method that used low-molecular-weight tertiary amine.

Acid salt solution 235-11 from the amine dewatering section (e.g. 230 in FIG. 1) is about 20% acid salt with the remainder water. A lower water content is possible if the acid salt solution is additionally dewatered using multiple-effect evaporators. Acid salt solution 235-11 flows into contactor 600-11 which contacts the acid salt solution with a carbon-dioxide-rich stream 602-11 and a high-molecular-weight tertiary amine 643-11. Suitable high-molecular-weight amines include higher alkanes (e.g., tributylamine, trioctylamine) and triethanol amine. Although triethanol amine itself does not have a high molecular weight, it reacts with the organic acids to make esters that do have very high molecular weights. Triethanol amine is preferred because it is inexpensive and widely used in natural gas processing. The high-molecular-weight tertiary amine 643-11, acid salt solution 235-11, and carbon-dioxide-rich gas 602-11 are agitated with mixer 605-11 to ensure good contact of all species. A reaction occurs in which the calcium in stream 235-11 reacts with the carbon dioxide in stream 602-11 and precipitates as calcium carbonate allowing the amine to form an amine/acid complex.

$$CaA_2 + CO_2 + 2R'_3N + H_2O \rightarrow CaCO_3 + 2R'_3NHA$$

To ensure that none of the high-molecular-weight tertiary amine leaves contactor 600-11, contacting trays may be placed above the mixer. Exhaust gases exit in stream 610-11.

The calcium carbonate precipitate is removed in solids separator 620-11 (e.g., filter, cyclone, or centrifuge). Using solids separator 625-11, low-molecular-weight tertiary amine 800 from the amine dewatering system (e.g., 230 in FIG. 1) removes residual amine/acid complex. Solids separator 620-11 and 625-11 could be the same piece of equipment; for ease of understanding, the filtration modes and washing operating modes shown in FIG. 11 use different pieces of equipment. Washed calcium carbonate 626-11 must have the volatile low-molecular-weight tertiary amine removed from the calcium carbonate using drier 680-11. Motor 685-11 rotates impellor 690-11 to ensure good contact between the superheated steam and the solids. The exiting steam is sent to the amine dewatering system (e.g., 230 in FIG. 1) to provide energy for water to phase out of the amine.

If the above reaction is performed with a large amount of water, the water may be removed from stream 629-11 using multiple-effect evaporator 630-11. Three effects are shown in FIG. 11, but fewer or more may be employed depending upon economic concerns. To promote energy efficiency, streams 633-11 and 634-11 may be returned to the amine dewatering system. Vapors 634-11 exiting the multiple-effect evaporator can be used to supply the latent heat needed to phase separate the water and amine in the amine dewatering system.

Liquid stream 632-11 exiting multiple-effect evaporator 630-11 contains high-molecular-weight tertiary amine/acid complex and small amounts of water. In distillation column 635-11, the water is removed. Distillation column 635-11 is operated below the temperature at which the amine/acid complex decomposes. Superheated steam (or an inert gas) is added at the bottom of the column to promote good mass transfer on the trays. By drawing a side stream of liquid from trays on the column (not shown in FIG. 11), and supplying heat using a heat exchanger, water will evaporate leaving the high-molecular-weight tertiary amine/acid complex primarily in the liquid phase. Partial condenser 638-11 allows water reflux to be added to the distillation column to ensure little amine exits the top. To promote energy efficiency, vapors 700-11 from the partial condenser may be directed to the amine dewatering system (e.g., 230 in FIG. 1). Distillation column 635-11 can be eliminated if water can be tolerated in the downstream processing steps.

The bottoms 641-11 from distillation column 635-11 contain high-molecular-weight tertiary amine/acid complex. They are preheated in countercurrent heat exchanger 640-11 and are introduced to reactive distillation column 645-11. This column is operated above the decomposition temperature of the amine/acid (approximately 170° C.) where the following reaction occurs $$R'_3NHA \rightarrow R'_3N + HA$$

Volatile acid 705-11 exits the top of the column. Condenser 639-11 allows reflux to be added to the distillation column to ensure little amine exits the top. To promote energy efficiency, the latent heat from condenser 639-11 may be rejected to the amine dewatering system (e.g., 230 in FIG. 1).

High-molecular-weight tertiary amine 643-11 exiting the bottom of reactive distillation column 645-11 is cooled in countercurrent heat exchanger 640-11 and sent to contactor 600-11 to react with the calcium salt of the acid.

A small stream 710-11 is withdrawn from the bottoms of reactive distillation column 645-11 to recover precipitated minerals that accumulate. Solids separator 715-11 (e.g., filter, hydroclone, centrifuge) removes the solids from the high-molecular-weight tertiary amine. These solids are sent to solids separator 720-11 where they are washed with low-molecular-weight tertiary amine 725-11. Solids separator 715-11 and 720-11 could be the same piece of equipment; for case of understanding, the filtration modes and washing operating modes shown in FIG. 11 use different pieces of equipment. Liquid stream 765-11 exiting solids separator 720-11 is a mixture of high-molecular-weight tertiary amine and low-molecular-weight tertiary amine. This stream is preheated using countercurrent heat exchanger 730-11 and sent to distillation column 735 which separates the two amines. Partial condenser 740-11 condenses some of the low-molecular-weight tertiary amine and refluxes it back to the distillation column to remove high-molecular-weight tertiary amine from the tops. The vapors exiting distillation column 735-11 are sent to the amine dewatering system (e.g., 230 in FIG. 1) to provide energy for phasing water out of the amine.

Washed solids 770-11 are directed to drier 745-11 where they are contacted with superheated steam that strips off residual low-molecular-weight tertiary amine. To ensure good 5 contact of solids with the superheated steam, the contents are agitated using impellor 755-11 driven by motor 750-11. Dry minerals 760-11 exit the drier 745-11. If necessary, a small amount of acid (e.g., sulfuric acid) can be added to ensure that all salt cations (e.g., K+) have an accompanying anion (e.g., $SO_4^{2-}$).

Figure 12:
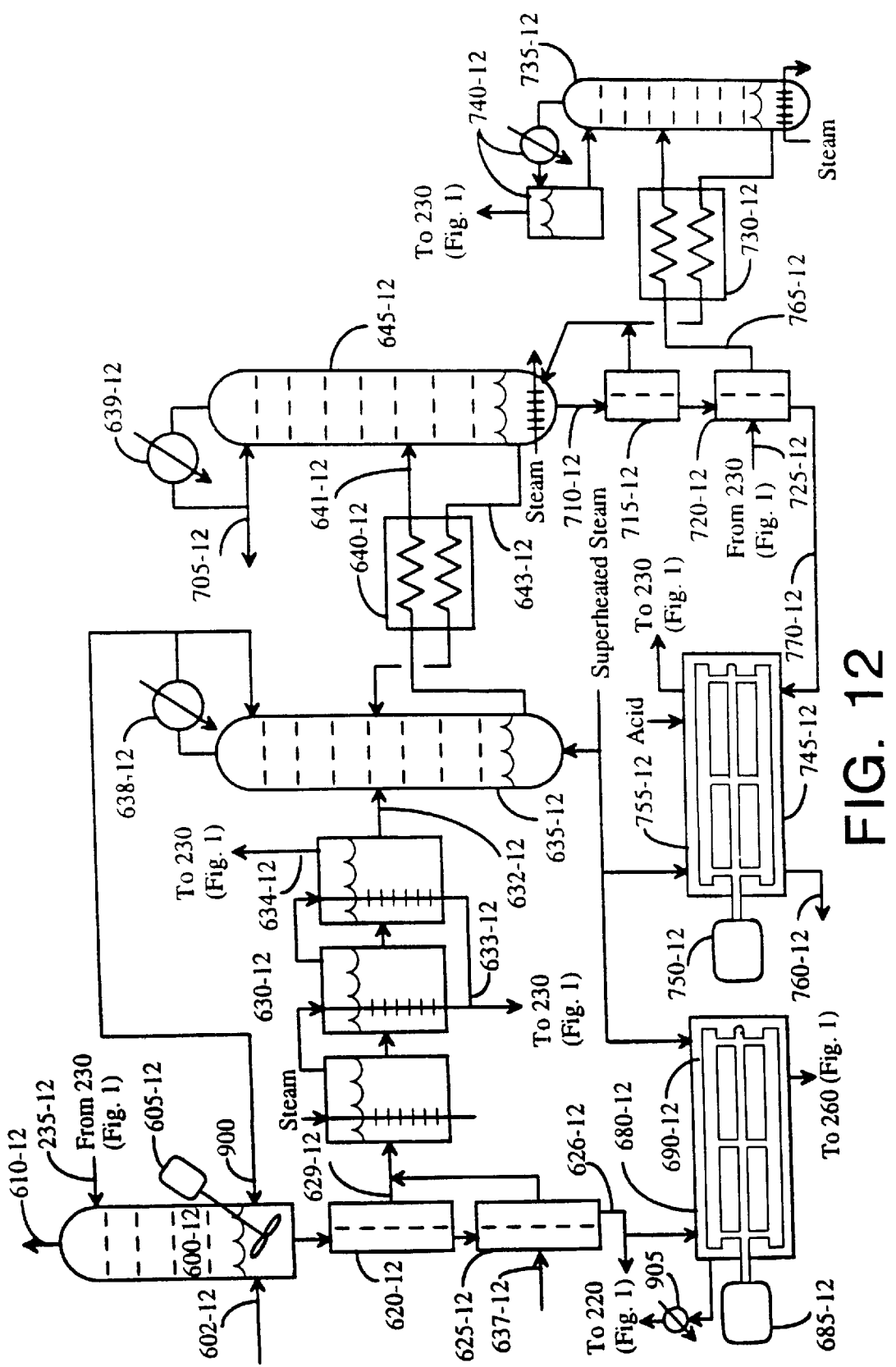
FIG. 12 shows a schematic representation of Recovery Method R-E.

Still another alternative embodiment is shown in FIG. 12 (Recovery Method R-E) which allows low-boiling acids (e.g., acetic) to be "sprung" from calcium salts of acids. This method is similar to Recovery Method R-C, except ammonia is substituted for the low-molecular-weight tertiary amine. The advantage is that ammonia is inexpensive, so losses can be tolerated. Also, because ammonia can be added to the fermentor as a nitrogen source, any ammonia losses that are directed to the fermentor (e.g., 220 in FIG. 1) have no cost because ammonia would be added to the fermentor anyway.

Acid salt solution 235-12 from the amine dewatering section (e.g. 230 in FIG. 1) is about 20% acid salt with substantially all of the remainder water. A lower water content is possible if the acid salt solution is additionally dewatered using multiple-effect evaporators. It flows into contactor 600-12 which contacts the acid salt solution with a carbon-dioxide-rich stream 602-12 and ammonia 900. Ammonia 900, acid salt solution 235-12, and carbon-dioxide-rich gas 602-12 are agitated with mixer 605-12 to ensure good contact of all species. A reaction occurs in which the calcium in stream 235-12 reacts with the carbon dioxide in stream 602-12 and precipitates as calcium carbonate allowing the ammonia to form an ammonia/acid complex.

$$CaA_2 + CO_2 + 2NH_3 + H_2O \rightarrow CaCO_3 + 2NH_4A$$

To ensure that little of the volatile ammonia leaves contactor 600-12, contacting trays may be placed above the mixer. Exhaust gases leave in stream 610-12.

The calcium carbonate precipitate is removed in solids separator 620-12 (e.g., filter, cyclone, or centrifuge). Using solids separator 625-12, wash water 637-12 removes residual ammonia/acid complex. Solids separator 620-12 and 625-12 could be the same piece of equipment; for ease of understanding, the filtration modes and washing operating modes shown in FIG. 12 use different pieces of equipment. Washed calcium carbonate 626-12 may be sent directly to the fermentor (e.g., 220 in FIG. 1) because there is no penalty associated with returning ammonia to the fermentor. For calcium carbonate 626-12 being sent to the lime kiln (e.g. 260 in FIG. 1) it is necessary to remove the residual ammonia using drier 680-12. Motor 685-12 rotates impellor 690-12 to ensure good contact between the superheated steam and the solids. The exiting steam is condensed in condenser 905. To promote energy efficiency, the heat is rejected to amine dewatering system (e.g. 230 in FIG. 1) to provide the latent heat needed to cause phase separation between the amine and water.

If the above reaction is performed with a large amount of water, the water may be removed from stream 629-12 using multiple-effect evaporator 630-12. Three effects are shown in FIG. 12, but fewer or more may be employed depending upon economic concerns. Any ammonia in streams 633-12 and 634-12 may be separated from the water by stripping. Alternatively, to promote energy efficiency, streams 633-12 and 634-12 may be returned to the amine dewatering system (e.g. 230 in FIG. 1). The vapors exiting the multiple-effect evaporator 634-12 can be used to supply the latent heat needed to phase separate the water and amine in the amine dewatering system (e.g., 230 in FIG. 1).

Liquid stream 632-12 exiting multiple-effect evaporator 630-12 contains ammonia/acid complex and small amounts of water. In distillation column 635-12, the ammonia is replaced with a high-molecular-weight amine $$NH_4A + R'_3N \rightarrow R'_3NHA + NH_3$$

Suitable high-molecular-weight amines include higher alkanes (e.g., tributylamine, trioctylamine) and triethanol amine. Although triethanol amine itself does not have a high molecular weight, it reacts with the organic acids to make esters that do have very high molecular weights. Triethanol amine is preferred because it is inexpensive and widely used in natural gas processing.

Distillation column 635-12 is operated well below the temperature at which the ammonia/acid complex decomposes. Because ammonia is not a tertiary amine, amides potentially may form; thus, if necessary, distillation column 635-12 could be operated under vacuum to keep the temperature as low as possible to avoid amide formation. Superheated steam (or an inert gas) is added at the bottom of the column to promote good mass transfer on the trays. By drawing a side stream of liquid from trays on the column (not shown in FIG. 12), and supplying heat using a heat exchanger, water and ammonia will evaporate leaving the high-molecular-weight tertiary amine/acid complex primarily in the liquid phase. Condenser 638-12 allows reflux to be added to the distillation column to ensure little high-molecular-weight amine exits the top. To promote energy efficiency, the heat from condenser 638-12 may be directed to the amine dewatering system (e.g. 230 in FIG. 1).

Bottoms 641-12 from distillation column 635-12 contain high-molecular-weight tertiary amine/acid complex. They are preheated in countercurrent heat exchanger 640-12 and are introduced to reactive distillation column 645-12. This column is operated above the decomposition temperature of the amine/acid (approximately 170° C.) where the following reaction occurs $$R'_3NHA \rightarrow R'_3N + HA$$

Volatile acid 705-12 exits the top of the column. Condenser 639-12 allows reflux to be added to the distillation column to ensure little amine exits the top. To promote energy efficiency, the latent heat from condenser 639-12 may be rejected to the amine dewatering system (e.g. 230 in FIG. 1).

The high-molecular-weight tertiary amine 643-12 exiting the bottom of the reactive distillation column 645-12 is cooled in countercurrent heat exchanger 640-12 and sent to distillation column 635-12 to exchange with the ammonia.

A small stream 710-12 is withdrawn from the bottoms of reactive distillation column 645-12 to recover precipitated minerals that accumulate. Solids separator 715-12 (e.g., filter, hydroclone, centrifuge) removes the solids from the high-molecular-weight tertiary amine. These solids are sent to solids separator 720-12 where they are washed with low-molecular-weight tertiary amine 725-12. Solids separator 715-12 and 720-12 could be the same piece of equipment; for ease of understanding, the filtration modes and washing operating modes shown in FIG. 12 use different pieces of equipment. Liquid stream 76512 exiting solids separator 720-12 is a mixture of high-molecular-weight tertiary amine and low-molecular-weight tertiary amine. This stream is preheated using countercurrent heat exchanger 730-12 and sent to distillation column 735-12 which separates the two amines. Partial condenser 740-12 condenses some of the low-molecular-weight tertiary amine and refluxes it back to the distillation column to remove high-molecular-weight tertiary amine from the tops. The vapors exiting distillation column 735-12 are sent to the amine dewatering system (e.g. 230 in FIG. 1) to provide energy for phasing water out of the amine. Typically, the low-molecular-weight amine will be the same as that used in the amine dewatering system (e.g. 230 in FIG. 1).

Washed solids 770-12 are directed to drier 745-12 where they are contacted with superheated steam that strips off residual low-molecular-weight tertiary amine. To ensure good contact of solids with the superheated steam, the contents are agitated using impellor 755-12 driven by motor 756-12. Dry minerals 760-12 exit drier 745-12. If necessary, a small amount of acid (e.g., sulfuric acid) can be added to ensure that all salt cations (e.g., $K^+$) have an accompanying anion (e.g., $SO_4^{2-}$).

All Recovery Methods R-A to R-E are discussed herein in terms of a single product (e.g., acetic acid, acetone). Because fermentation liquids rarely contain a single dissolved component, it will be necessary to further distill the recovered products if a pure product is desired. This may, or may not, be necessary. For example, if the ketone products from Recovery Method R-A are to be hydrogenated to alcohols that are blended into motor fuel, the mixed ketone products are sufficient. However, if chemical-grade acetone is going to be sold, it will have to be separated from the higher ketones (e.g., methyl ethyl ketone, diethyl ketone) using distillation or other appropriate technologies.

A preferred mode for the processes presented here uses a low-MW amine to remove water from fermentation liquid in the amine dewatering system (e.g. 230 in FIG. 1). The advantages of this method compared to others were already discussed. Recovery Methods R-A to R-E integrate well with the concentration section of such a plant because waste heat and streams that contain low-MW tertiary amine are returned to the amine dewatering system.

All of the processes described thus far neutralize the acids in the fermentor with lime or calcium carbonate. If the acids were neutralized with ammonia, then ammonium acetate (propionate, butyrate, lactate) would be produced in the concentration section of the plant rather than calcium acetate (propionate, butyrate, lactate). However, the amine dewatering system more selectively concentrates divalent ions (e.g., calcium) than monovalent ions (e.g., sodium, ammonium). Nonetheless, if ammonium were the cation, Recovery Method R-E would be employed (without lime kiln 260 (FIG. 1), contactor 600-12, and calcium carbonate filter 620-12).

EXAMPLES

In order to facilitate a more complete understanding of the invention, a number of specific Examples are provided below. However, the scope of the invention is not limited to specific embodiments disclosed in these Examples, which are for purposes of illustration only.

Example 1

Conversion of Biomass to Organic Acids

Fermentation F-A

Biomass (e.g., bagasse, grass, municipal solid waste) is placed in a tank. Warm water is added from a recycle stream. If desired, warm gases ($CO_2$, $N_2$ and $O_2$) from a recycle stream can be bubbled through the water to heat it further. Then lime is added to the biomass.

The lime/water/biomass slurry soaks for 1 to 24 hours while stirring. When the soak is complete, the lime water will be drained from the solid slurry. More lime may be removed by leaching the biomass with recycle water.

The lime-treated biomass is slowly added to a fermentor where anaerobic organisms convert the biomass to organic acids. These organisms are a mixed culture that may be obtained from many sources (e.g., cattle rumen, anaerobic sewage digesters). They produce a variety of products, but mainly acetic acid with lesser amounts of propionic and butyric acids. The ratio of these products depends on factors such as the microbial population, the pH, and temperature. Acetic acid dominates at temperatures above 55° C.

As the organic acids are formed, the pH lowers. The lime that was not recovered during the leaching process will act to neutralize the acids by forming calcium salts. The pH is further regulated by adding the lime water from the leaching. Alternatively, recycled calcium carbonate can be used. Generally, a pH near 6.2 is preferred, but pH range from about 5.5 to 7.0 is suitable.

Because there are no asepsis requirements (i.e. neither the feed nor vessels must be sterilized), recycle may be employed without risk of contamination. The fermentors will be operated in a continuous fashion. Cells may be recycled to maintain a high cell concentration in the fermentors which will reduce the required residence time. The solids concentration in the fermentor will be high (about 10–25%) to make the most efficient use of fermentor volume. If all the carbohydrates in the biomass were converted to organic acids, the concentration of organic acid salts would be about 8–20% which is much higher than can be tolerated by the microbes. To avoid this problem, the liquid is constantly removed from the fermentors to maintain the organic acid salt concentration below about 3.4%. A number of methods could be employed to separate the solids from the liquid (e.g., filters, settlers). For example, the slurry could be pumped through a hydroclone in which the centrifugal force of the swirling fluid separates the solids from the liquid. The liquid will still have some particles because the separation is not perfect; therefore, it can be further clarified by filtration through a sand filter, or similar device. When the sand filter is cleaned by backflushing, the solids are simply returned to the fermentors for further conversion to organic acids.

The biomass will be traveling through the fermentor train in essentially a plug flow. The carbohydrate content of the biomass will drop as it is converted to organic acids. Eventually, the solids will consist primarily of lignin, calcium carbonate, and cells. The cells can be recovered separately because they settle more slowly than the undigested solids and calcium carbonate. The remaining solids (lignin and calcium carbonate) can be burned in a lime kiln to supply process heat and convert the calcium carbonate into lime.

Example 2

Conversion of Biomass to Organic Acids

Fermentation F-B

This fermentation is similar to Fermentation A, except that both acetic acid and ethanol are produced simultaneously by thermophilic bacteria. The cellulytic organism *Clostridium thermocellum* is employed. It has a high cellulase activity and can convert hexoses into ethanol and acetic acid in approximately equal amounts. Because this organism is unable to utilize pentose sugars, *Clostridium thermosaccharolyticum, C. thermohydrosulfuricum*, or *Thermoanaerobacter ethanolicus* may be cocultured with the *C. thermocellum*. The ethanol is recovered by distillation, whereas the acetic acid is concentrated and recovered by the methods discussed below. If the organisms are more tolerant of acetate ions than ethanol, much of the distillation column bottoms can be recycled to the fermentor allowing the acids to build to higher concentrations.

This process requires asepsis because a pure culture (or co-culture) is being maintained. The lime treatment may be sufficient to sterilize both the biomass and water.

However, if contamination is a problem, it will be necessary to sterilize the biomass by direct steam injection. The water can be sterilized using conventional sterilization equipment (i.e. countercurrent heat exchangers with a high-temperature holding section). The fermentor may be operated in either a batch or continuous mode, but the batch mode is likely to have fewer contamination problems.

All of the processes described neutralize the acids in the fermentor with lime. If the acids were neutralized with ammonia, then ammonium acetate (propionate, butyrate, lactate) would be produced in the concentration section of the plant rather than calcium acetate (propionate, butyrate, lactate).

Example 3

Concentration by Extraction With Low-Molecular-Weight Amines

The fermentation liquid from Fermentation F-A or Fermentation F-B contains about 34% organic acid salts, therefore there are about 25 to 33 parts of water per part of organic acid. This water must be removed to recover the product which may be accomplished by extracting the water from the fermentation liquid. Low-molecular-weight (low-MW) secondary and tertiary amines with about five to six carbon atoms per molecule are preferred. There are many candidate amines (as described Davison et al.), the preferred amines are diisopropyl, triethyl, and methyldiethyl. Mixtures of triethyl and methyldiethyl amines are very useful, because the operating temperature of the extractor may be regulated by changing the triethyl:methyldiethyl ratio.

Using lime, the fermentation liquid is adjusted to about pH 11 to prevent the low-MW amines from reacting with acids in the fermentation liquid. This alkaline liquid is countercurrently contacted with the low-MW amine. Because there is a heat of mixing, cooling is needed to maintain the desired temperature. If the extraction is performed at a low temperature (e.g., 40° C.) the heat of mixing must be rejected to cooling water. However, if the extraction is performed at high temperatures (e.g., 60° C.), then this heat might be useful as very low-grade process heat in the final stage of a multi-effect evaporator. The extraction temperature will be essentially the same as the fermentor temperature to eliminate heating (or cooling) of the fermentation liquid prior to entering the extractor. A preliminary engineering study indicates that a five-stage extractor will remove 86% of the water, producing an aqueous product stream with 20% salt concentration.

The low-MW amine stream with the extracted water is then heated to about 20° C. higher than the extractor temperature. This causes the water to separate from the amines because they have reduced miscibility at higher temperatures. Much of the 20° C. temperature rise is achieved by countercurrently contacting the incoming amine/water solution with outgoing amine. The remainder of the temperature rise is achieved by directly injecting steam (that contains some low-MW amines) into the incoming solution. The water/amine separation is not perfect, because the water phase contains about 5% (w/w) amine, and the amine phase contains about 5% (w/w) water. The amine phase is simply recycled to the extractor whereas the water phase must be stripped of the amine. The stripper may be operated at a high pressure so the exiting vapors may be used for process heat. Much of these vapors will be directly injected into the amine separator to complete the needed 20° C. temperature rise. The stripping efficiency is greatly improved by adjusting to about pH 11 using lime. The aqueous phase exiting the extractor may be further concentrated in a multiple-effect evaporator. Some of the heat required by the evaporators may be supplied from the stripping column vapors.

Example 4

Conversion of Biomass to Liquid Fuel

This recovery method produces ketones (e.g., acetone, methyl ethyl ketone, diethyl ketone, etc.) from organic acid salts (e.g., acetate, propionate, butyrate). Although many organic acid salts are present in the mixtures, the process as it affects calcium acetate will be described in this illustrative example. Calcium acetate can be converted almost stoichiometrically to acetone and calcium carbonate by pyrolyzing at 400–450° C. It is important to remove the acetone as soon as it is formed because it will decompose at those high temperatures.

An aqueous stream containing 20% calcium salts of organic acids is produced as described for Example 3. Multi-effect evaporators can be used in the concentration section to remove so much water that the calcium acetate precipitates. The solids are removed by filtration and the liquid is returned to the multi-effect evaporators. The solids are dried by blowing hot gases from the lime kiln through a drier, i.e. a horizontal tank with an internal mixer that allows good contact between the solids and hot gases. Alternatively, the solids can be dried using superheated steam.

The dry calcium acetate is transported to the pyrolyzer lock hopper using a screw conveyor. When the lock hopper opens, the calcium acetate enters the thermal convertor where it is mixed with a hot transfer medium (e.g., glass beads). The calcium acetate reacts to form calcium carbonate and acetone. The acetone is cooled by contacting it with incoming calcium acetate, then it is condensed and recovered. The vapor pressure of acetone is fairly low if the acetone is condensed at low temperatures, thus allowing the thermal convertor to operate under -a vacuum. This ensures that the acetone has a short residence time in the thermal convertor. The required residence time of the solids is about 10 minutes (depending on the temperature) for a complete reaction. Because some noncondensibles may enter the thermal convertor, a small vacuum pump will be needed to remove them.

Calcium carbonate exiting the thermal convertor is separated from the heat transfer medium. The calcium carbonate may be sent to a lime kiln to regenerate lime or it may be added directly to the fermentor as a neutralizing agent. The heat transfer agent is heated by direct contact with hot gases, such as those exiting the lime kiln or a combustor.

Because biomass contains minerals (up to about 10% for some grasses and herbaceous crops), these minerals must be purged. Soluble minerals can be removed by pulling a side stream from the calcium carbonate and washing with water. Insoluble minerals can be recovered from the stream exiting the lime kiln by dissolving the lime in water and recovering the insoluble minerals. Calcium phosphate will be an important component of the insolubles. It can be acidified by adding sulfuric acid which will cause gypsum (calcium sulfate) to precipitate, allowing the phosphorous to be recovered as phosphoric acid. The minerals recovered from these side streams can be sold as fertilizer, so it is expected that this part of the plant will pay for itself with fertilizer sales.

The gases exiting the lime kiln are very hot (about 900° C.). These gases supply process thermal energy. High-pressure steam can be made from the hottest gases and used for making electricity. The lower temperature gases (about 550° C.) will heat the heat transfer medium. Then some low-pressure steam can be made to supply energy for the multi-effect evaporators. Finally the lowest temperature gases can be used to dry the VFA salts, heat water in the biomass soaking vessel or provided heat to the amine dewatering process.

The recovery methods are exemplified by a single product (e.g., acetic acid, acetone). However, fermentation liquids rarely contain a single dissolved component. Therefore, it will be necessary to further distill the recovered products if a pure product is desired. This may, or may not, be necessary. For example, if the ketone products are to be hydrogenated to alcohols that are blended into motor fuel, the mixed ketone products are sufficient. However, if chemical-grade acetone is going to be sold, it will have to be separated from the higher ketones (e.g., methyl ethyl ketone, diethyl ketone) using distillation or other appropriate technologies.

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons of skill in biochemical, chemical and fermentation engineering and/or related fields are intended to be within the scope of the invention, which is limited only by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

What is claimed is:

1. A process for recovering low-boiling acids from a concentrated solution of calcium salt of the acid comprising contacting a concentrated solution of calcium salt of low-boiling acids with a high-molecular-weight tertiary amine and carbon dioxide, forming calcium carbonate precipitate and a liquid solution containing high-molecular-weight tertiary amine/acid complex, washing the calcium carbonate precipitate with a volatile solvent to remove residual high-molecular-weight tertiary amine, drying the calcium carbonate precipitate to remove residual volatile solvent, and thermally breaking the high-molecular-weight tertiary amine/acid complex and allowing the nonvolatile high-molecular-weight tertiary amine to separate from volatile low-boiling acids.

2. The process of claim 1, wherein the volatile solvent is a low-molecular-weight amine.

3. The process of claim 2, wherein the same low-molecular-weight amine is used in an amine dewatering step to produce the concentrated solution of calcium salt of low-boiling acids.

4. The process of claim 1, wherein the high-molecular-weight tertiary amine/acid complex is thermally broken in a reactive distillation column.

5. The process of claim 1, wherein water is removed using multiple-effect evaporation or distillation or both prior to thermally breaking the high-molecular-weight tertiary amine/acid complex.

6. The process of claim 1, wherein salt precipitate is separated from the high-molecular-weight tertiary amine, washed with a volatile solvent, and dried to remove volatile low-molecular-weight tertiary amine, the recovered wash fluid being separated using distillation.

7. The process of claim 6, wherein the volatile solvent is a low-molecular-weight amine.

8. The process of claim 6, wherein the volatile solvent is the same low-molecular-weight amine used in the amine dewatering system to produce the concentrated salt solution.

* * * * *